US008178675B2

(12) United States Patent
Romantsev et al.

(10) Patent No.: US 8,178,675 B2
(45) Date of Patent: May 15, 2012

(54) COMPOUNDS FOR THE TREATMENT OF METABOLIC DISORDERS

(75) Inventors: Fedor Evgenievich Romantsev, Gaithersburg, MD (US); Shalini Sharma, Gaithersburg, MD (US); Reid W. von Borstel, Potomac, MD (US); Stephen D. Wolpe, Boyds, MD (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 856 days.

(21) Appl. No.: 12/092,932

(22) PCT Filed: Nov. 9, 2006

(86) PCT No.: PCT/US2006/060727
§ 371 (c)(1),
(2), (4) Date: Sep. 10, 2008

(87) PCT Pub. No.: WO2007/056771
PCT Pub. Date: May 18, 2007

(65) Prior Publication Data
US 2009/0203793 A1    Aug. 13, 2009

Related U.S. Application Data

(60) Provisional application No. 60/734,803, filed on Nov. 9, 2005.

(51) Int. Cl.
C07D 213/00 (2006.01)
C07D 211/79 (2006.01)
C07C 69/76 (2006.01)
C07C 229/00 (2006.01)

(52) U.S. Cl. ............ 546/1; 546/329; 560/8; 560/19; 560/39; 560/75

(58) Field of Classification Search ............. 546/1, 329; 560/8, 19, 39, 75
See application file for complete search history.

(56) References Cited

U.S. PATENT DOCUMENTS

| 4,221,919 | A  | 9/1980  | Grimova et al. |
| 5,298,511 | A  | 3/1994  | Waterson |
| 6,858,602 | B2 | 2/2005  | Sharma et al. |
| 6,916,848 | B2 | 7/2005  | Sharma |
| 6,924,314 | B2 | 8/2005  | Sharma et al. |
| 6,946,491 | B2 | 9/2005  | Sharma et al. |
| 7,012,071 | B2 | 3/2006  | Sharma et al. |
| 7,041,659 | B2 | 5/2006  | Sharma |
| 7,045,541 | B2 | 5/2006  | Sharma |
| 7,101,910 | B2 | 9/2006  | Sharma |
| 7,329,782 | B2 | 2/2008  | Sharma et al. |
| 7,361,686 | B2 | 4/2008  | Hodge et al. |
| 7,649,110 | B2 | 1/2010  | Akerman et al. |
| 2003/0187068 | A1 | 10/2003 | Miyachi et al. |
| 2004/0043994 | A1 | 3/2004  | Khanna et al. |
| 2005/0090555 | A1 | 4/2005  | Sharma et al. |
| 2006/0014784 | A1 | 1/2006  | Hodge et al. |
| 2006/0035970 | A1 | 2/2006  | Hodge et al. |
| 2006/0247309 | A1 | 11/2006 | Hodge et al. |
| 2007/0105958 | A1 | 5/2007  | Sharma et al. |
| 2007/0173544 | A1 | 7/2007  | Hodge et al. |
| 2007/0249696 | A1 | 10/2007 | Sharma et al. |
| 2007/0249719 | A1 | 10/2007 | Sharma et al. |
| 2007/0265322 | A1 | 11/2007 | Sharma et al. |
| 2007/0282003 | A1 | 12/2007 | Sharma et al. |
| 2008/0015209 | A1 | 1/2008  | Sharma et al. |
| 2008/0015254 | A1 | 1/2008  | Sharma et al. |
| 2008/0021109 | A1 | 1/2008  | Sharma et al. |
| 2008/0027229 | A1 | 1/2008  | Hodge et al. |

FOREIGN PATENT DOCUMENTS

| FR | 5.035 M       | 5/1967  |
| JP | 2004123643    | 4/2004  |
| RU | 2235094 C2    | 8/2004  |
| WO | 99/19313 A1   | 4/1999  |
| WO | 02083616 A1   | 10/2002 |
| WO | 02/100341 A2  | 12/2002 |
| WO | 2004/073611 A2| 9/2004  |
| WO | 2004/091486 A2| 10/2004 |
| WO | 2005/019151 A1| 3/2005  |
| WO | 2005/086661 A2| 9/2005  |

OTHER PUBLICATIONS

Peretto, et al. "Synthesis and Biological Activity of Flurbiprofen Analogues as Selective Inhibitors of B-Amyloid1-42 Secretion", J. Med. Chem, vol. 48, pp. 5705-5720, 2005.
Nomura, et al., "Design, Synthesis, and Evaluation of Substituted Phenylpropanoic Acid Derivatives as Human peroxisome Proliferator Activated Receptor Activators. Discovery of Potent and Human Peroxisome Proliferator Activated Receptor x Subtype-Selective Activators", J. Med. Chem. vol. 46, pp. 3581-3599, 2003.
Younis, et al., "The prevention of type 2 diabetes mellitus: recent advances", QJ Med., vol. 97, pp. 451-455, 2004.
Goff, et al., "Prevention of Cardiovascular Disease in Persons with type 2 diabetes Mellitus: Current Knowledge and Rational for the Action to Control Cardiovascular Risk in Diabetes (ACCORD) Trial", Am J Cardiol., 99(12A): S4-S20, 2007. (Abstract).
Knowler, et al,. "Perspectives in Diabetes: Preventing Non-Insulin-Dependent Diabetes", Diabetes, vol. 44, pp. 483-488, 1995.
Pending (as of Mar. 24, 2008) claims from U.S. Appl. No. 11/772,515.
Pending (as of Mar. 24, 2008) claims from U.S. Appl. No. 11/772,520.
Pending (as of Mar. 24, 2008) claims from U.S. Appl. No. 11/772,560.
Pending (as of Sep. 25, 2008) claims from U.S. Appl. No. 12/294,530.
Pending (as of Jul. 14, 2008) claims from U.S. Appl. No. 12/160,854.
Pending (as of Jul. 28, 2008) claims from U.S. Appl. No. 12/162,397.
Pending (as of Jul. 14, 2008) claims from U.S. Appl. No. 12/160,857.
Pending (as of Aug. 18, 2008) claims from U.S. Appl. No. 12/160,808.
Pending (as of Aug. 13, 2008) claims from U.S. Appl. No. 12/279,247.
Abstract No. 2003-019191, corresponding to International patent No. WO02/083616 published Oct. 24, 2002. (XP-002575893).
Abstract No. 2004-344526, corresponding to Japanese patent No. 2004123643 published Apr. 4, 2004. (XP-002575894).

Primary Examiner — Kevin E Weddington
(74) Attorney, Agent, or Firm — Lewis J. Kreisler

(57) ABSTRACT

Agents useful for the treatment of various metabolic disorders, such as insulin resistance syndrome, diabetes, hyperlipidemia, fatty liver disease, cachexia, obesity, atherosclerosis and arteriosclerosis are disclosed as Formula (I).

3 Claims, 1 Drawing Sheet

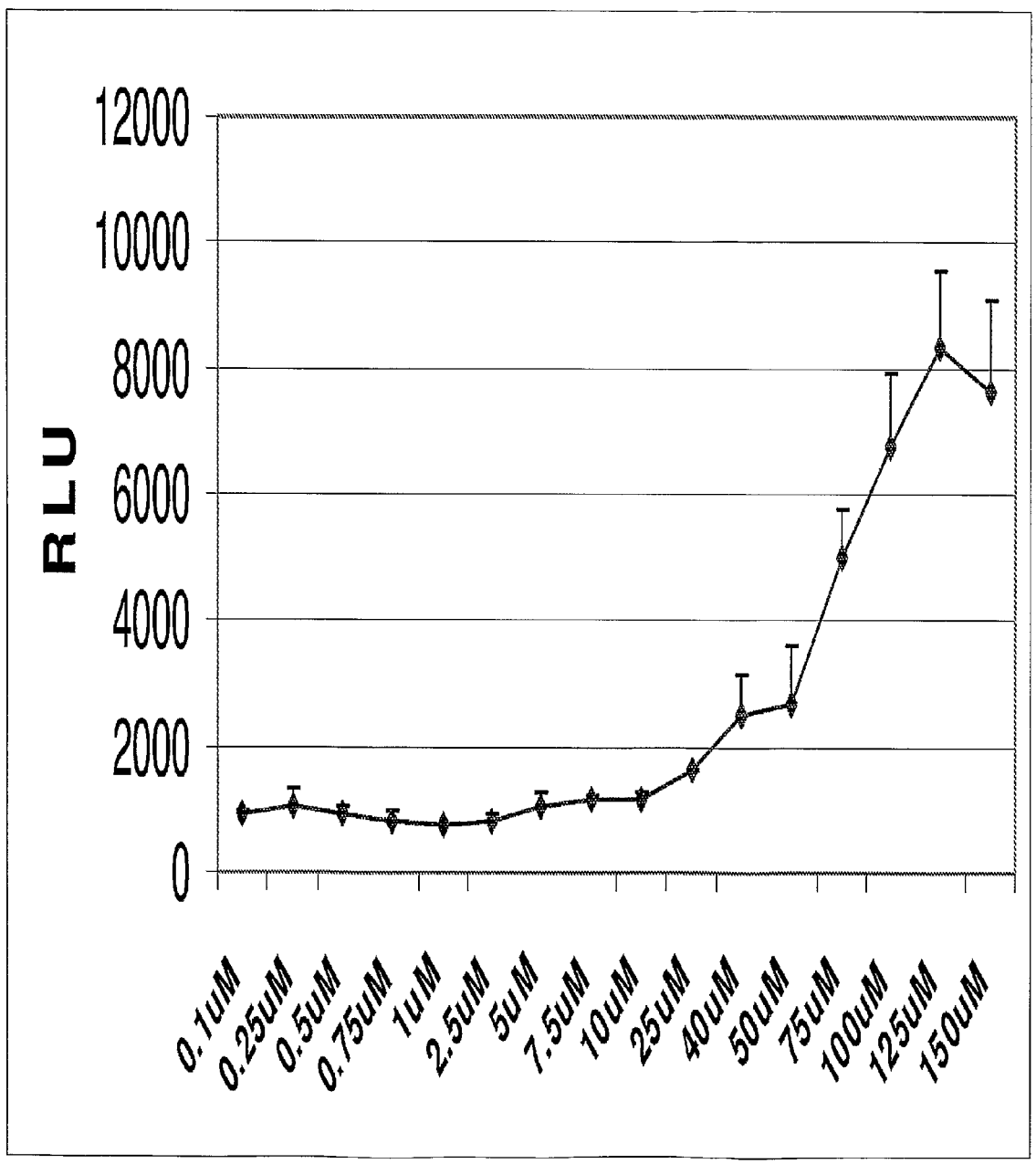

COMPOUNDS FOR THE TREATMENT OF METABOLIC DISORDERS

CROSS-REFERENCE TO RELATED APPLICATIONS

This application claims the priority of U.S. Provisional Patent Application No. 60/734,803, filed Nov. 9, 2005, the contents of which are incorporated herein by reference.

BACKGROUND OF THE INVENTION

Diabetes mellitus is a major cause of morbidity and mortality. Chronically elevated blood glucose leads to debilitating complications: nephropathy, often necessitating dialysis or renal transplant; peripheral neuropathy; retinopathy leading to blindness; ulceration of the legs and feet, leading to amputation; fatty liver disease, sometimes progressing to cirrhosis; and vulnerability to coronary artery disease and myocardial infarction.

There are two primary types of diabetes. Type I, or insulin-dependent diabetes mellitus (IDDM) is due to autoimmune destruction of insulin-producing beta cells in the pancreatic islets. The onset of this disease is usually in childhood or adolescence. Treatment consists primarily of multiple daily injections of insulin, combined with frequent testing of blood glucose levels to guide adjustment of insulin doses, because excess insulin can cause hypoglycemia and consequent impairment of brain and other functions.

Type II, or noninsulin-dependent diabetes mellitus (NIDDM) typically develops in adulthood. NIDDM is associated with resistance of glucose-utilizing tissues like adipose tissue, muscle, and liver, to the actions of insulin. Initially, the pancreatic islet beta cells compensate by secreting excess insulin. Eventual islet failure results in decompensation and chronic hyperglycemia. Conversely, moderate islet insufficiency can precede or coincide with peripheral insulin resistance. There are several classes of drugs that are useful for treatment of NIDDM: 1) insulin releasers, which directly stimulate insulin release, carrying the risk of hypoglycemia; 2) prandial insulin releasers, which potentiate glucose-induced insulin secretion, and must be taken before each meal; 3) biguanides, including metformin, which attenuate hepatic gluconeogenesis (which is paradoxically elevated in diabetes); 4) insulin sensitizers, for example the thiazolidinedione derivatives rosiglitazone and pioglitazone, which improve peripheral responsiveness to insulin, but which have side effects like weight gain, edema, and occasional liver toxicity; 5) insulin injections, which are often necessary in the later stages of NIDDM when the islets have failed under chronic hyperstimulation.

Insulin resistance can also occur without marked hyperglycemia, and is generally associated with atherosclerosis, obesity, hyperlipidemia, and essential hypertension. This cluster of abnormalities constitutes the "metabolic syndrome" or "insulin resistance syndrome". Insulin resistance is also associated with fatty liver, which can progress to chronic inflammation (NASH; "nonalcoholic steatohepatitis"), fibrosis, and cirrhosis. Cumulatively, insulin resistance syndromes, including but not limited to diabetes, underlie many of the major causes of morbidity and death of people over age 40.

Despite the existence of such drugs, diabetes remains a major and growing public health problem. Late stage complications of diabetes consume a large proportion of national health care resources. There is a need for new orally active therapeutic agents which effectively address the primary defects of insulin resistance and islet failure with fewer or milder side effects than existing drugs.

Currently there are no safe and effective treatments for fatty liver disease. Therefore such a treatment would be of value in treating this condition.

WO 02/100341 (Wellstat Therapeutics Corp.) and WO 04/073611 (Wellstat Therapeutics Corp.) disclose certain compounds substituted by two hydrogens at the final position of the acid, for example 4-(3-(2,6-Dimethylbenzyloxy)phenyl)-butyric acid and 3-(2,6-Dimethylbenzyloxy)phenylacetic acid. WO 04/091486 (Wellstat Therapeutics Corp.) discloses certain compounds substituted by hydroxy at the final position of the acid, for example 4-(3-(2,6-Dimethylbenzyloxy)-phenyl)-4-hydroxybutanoic acid. The aforementioned publications do not disclose any compounds within the scope of Formula I shown below, in which the final position of the acid is alkyl-substituted.

SUMMARY OF THE INVENTION

This invention provides a biologically active agent as described below. This invention provides the use of the biologically active agent described below in the manufacture of a medicament for the treatment of insulin resistance syndrome, diabetes, cachexia, hyperlipidemia, fatty liver disease, obesity, atherosclerosis or arteriosclerosis. This invention provides methods of treating a mammalian subject with insulin resistance syndrome, diabetes, cachexia, hyperlipidemia, fatty liver disease, obesity, atherosclerosis or arteriosclerosis comprising administering to the subject an effective amount of the biologically active agent described below. This invention provides a pharmaceutical composition comprising the biologically active agent described below and a pharmaceutically acceptable carrier.

The biologically active agent in accordance with this invention is a compound of Formula I:

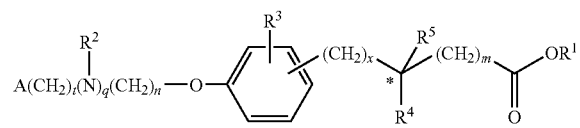

Formula I wherein n is 1 or 2; one of m and x is 0 and the other is 0, 1, 2, 3, or 4; q is 0 or 1; t is 0 or 1; $R^2$ is alkyl having from 1 to 3 carbon atoms; $R^3$ is hydrogen, halo, alkyl having from 1 to 3 carbon atoms, or alkoxy having from 1 to 3 carbon atoms; one of $R^4$ and $R^5$ is alkyl having from 1 to 3 carbon atoms and the other is hydrogen or alkyl having from 1 to 3 carbon atoms; A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; and $R^1$ is hydrogen or alkyl having 1 or 2 carbon atoms. Alternatively, when $R^1$ is hydrogen, the biologically active agent can be a pharmaceutically acceptable salt of the compound of Formula I.

The biologically active agents described above have activity in one or more of the biological activity assays described below, which are established animal models of human diabetes and insulin resistance syndrome. Therefore such agents would be useful in the treatment of diabetes and insulin resistance syndrome. All of the exemplified compounds that were tested demonstrated activity in at least one of the biological activity assays in which they were tested.

BRIEF DESCRIPTION OF THE FIGURE

FIG. 1: Dose-response curve for Compound CW in human PPARα transactivation assay

DETAILED DESCRIPTION OF THE INVENTION

Definitions

As used herein the term "alkyl" means a linear or branched-chain alkyl group. An alkyl group identified as having a certain number of carbon atoms means any alkyl group having the specified number of carbons. For example, an alkyl having three carbon atoms can be propyl or isopropyl; and alkyl having four carbon atoms can be n-butyl, 1-methylpropyl, 2-methylpropyl or t-butyl.

As used herein the term "halo" refers to one or more of fluoro, chloro, bromo, and iodo.

As used herein the term "perfluoro" as in perfluoromethyl or perfluoromethoxy, means that the group in question has fluorine atoms in place of all of the hydrogen atoms.

As used herein "Ac" refers to the group $CH_3C(O)$—.

Certain chemical compounds are referred to herein by their chemical name or by the two-letter code shown below. Compounds CW, CX and DP are included within the scope of Formula I shown above.

CW 2-(3-(2,6-Dimethylbenzyloxy)-phenyl)-2-(R,S)-methylacetic acid
CX 2-(3-(2,6-Dimethylbenzyloxy)-phenyl)-2-(R,S)-ethylacetic acid
DP 3-(3-(2,6-Dimethylbenzyloxy)-phenyl)-2-(R,S)-methylpropanoic acid As used herein the transitional term "comprising" is open-ended. A claim utilizing this term can contain elements in addition to those recited in such claim.

COMPOUNDS OF THE INVENTION

The asterisk in the depiction of Formula I above indicates a chiral center. This invention provides the racemate, the (R) enantiomer, and the (S) enantiomer, of the compounds of Formula I, all of which are active. Mixtures of these enantiomers can be separated by using HPLC, for example as described in Chirality 11:420-425 (1999).

In an embodiment of the agent, use, method or pharmaceutical composition described in the Summary above x is 0 and m is 0, 1, 2, 3, or 4. In a more specific embodiment m is 0, 2 or 4. In another embodiment, m is 0 and x is 0, 1, 2, 3 or 4. In a more specific embodiment x is 0, 2, or 4.

In an embodiment of the agent, use, method or pharmaceutical composition described in the Summary above, n is 1; q is 0; t is 0; $R^3$ is hydrogen; and A is phenyl, unsubstituted or substituted by 1 or 2 groups selected from: halo, alkyl having 1 or 2 carbon atoms, alkoxy having 1 or 2 carbon atoms, and perfluoromethoxy. In a more specific embodiment, A is 2,6-dimethylphenyl. Examples of such compounds include Compounds CW, CX and DP.

In a preferred embodiment of the biologically active agent of this invention, the agent is in substantially (at least 98%) pure form.

Reaction Schemes

The biologically active agents of the present invention can be made in accordance with the following reaction schemes.

The compound of formula I where m is 0, x is 0 or 1, q is 0 or 1, t is 0 or 1, and n is 1 or 2, $R^2$ is alkyl having from 1 to 3 carbon atoms, $R^3$ is hydrogen, halo, alkoxy having from 1 to 3 carbon atoms or alkyl having from 1 to 3 carbon atoms, $R^4$ and $R^5$ is alkyl having 1 to 3 carbon atoms and the other is hydrogen or alkyl having 1 to 3 carbon atoms. $R^1$ is hydrogen or alkyl having from 1 to 2 carbon atoms, i.e. compounds of formula:

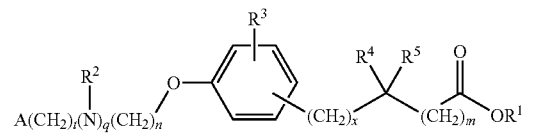

(I)

wherein A is described as above, can be prepared via reaction scheme of Scheme 1.

In the reaction scheme of Scheme 1, A, t, n, m, q, x, $R^2$, $R^3$, $R^4$ and $R^5$ are as above. $R^1$ is alkyl group having 1 to 2 carbon atoms. $R^7$ is alkyl group having 1 to 3 carbon atoms, and $Y^1$ is a halide.

The compound of formula II is alkylated with the compound of formula III via reaction of step (a) to produce the compound of formula IV. The reaction is carried out in a suitable solvent, such as tetrahydrofuran, tetrahydrofuran/1,3-dimethyl-3,4,5,6-tetrahydro-2(1H)-pyrimidinone, terahydrofuran/hexamethylphosphoramide and the like. Generally, the reaction is carried out in the presence of 2 to 3 molar equivalents of base to produce the compound of formula IV where $R^4$ is alkyl having 1 to 3 carbon atoms and $R^5$ is hydrogen or 4 to 6 molar equivalents of base to produce the compound of formula IV where $R^4$ and $R^5$ is alkyl having 1 to 3 carbon atoms. The conventional base for this purpose can be sodium hydride, potassium hydride, potassium bis(trimethylsilyl)amide, lithium bis(trimethylsilyl)amide, lithium diisopropylamide and the like. In carrying out this reaction it is generally preferred to utilize alkali metal salts of hexamethyldisilane. The reaction is carried out at temperatures from −78° C. to 25° C. Generally, the reaction requires 6 to 72 hours. The conventional techniques such as extraction, evaporation, chromatography and recrystallization can be utilized to purify the product.

The compound of formula IV is the compound of formula I where $R^1$ is alkyl group having from 1 to 2 carbon atoms. The compound of formula IV can be converted to the free acid i.e. the compound of formula I where $R^1$ is H by ester hydrolysis. Any conventional method of ester hydrolysis will produce the compound of formula I where $R^1$ is H.

If A is phenyl substituted by 1 or 2 groups of hydroxyl, it is generally preferred to protect the hydroxyl group of the compound of formula II. The suitable protecting group can be described in the Protective Groups in Organic Synthesis by T. Greene.

The protecting group can be deprotected utilizing suitable deprotecting reagents such as those described in Protective Groups in Organic Synthesis by T. Greene.

Reaction Scheme 1

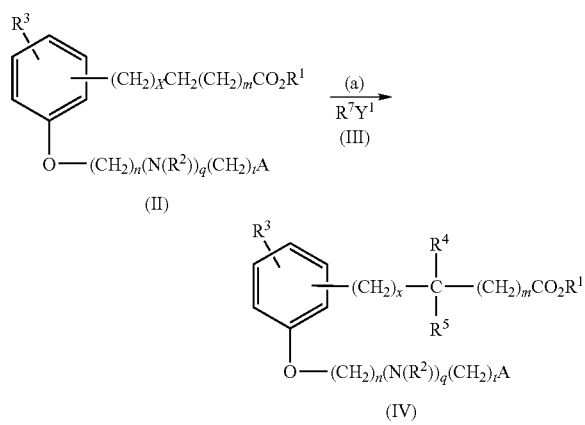

The compound of formula I where m is 1 to 4, x is 0, q is 0 or 1, t is 0 or 1, and n is 1 or 2, $R^2$ is alkyl having from 1 to 3 carbon atoms, $R^3$ is hydrogen, halo, alkoxy having from 1 to 3 carbon atoms or alkyl having from 1 to 3 carbon atoms, $R^4$ and $R^5$ is alkyl having 1 to 3 carbon atoms and the other is hydrogen or alkyl having 1 to 3 carbon atoms. $R^1$ is hydrogen or alkyl having from 1 to 2 carbon atoms, i.e. compounds of formula:

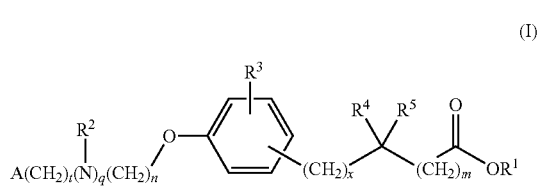

wherein A is described as above, can be prepared via reaction scheme of Scheme 2.

In the reaction scheme of Scheme 2, A, t, n, m, q, x, $R^2$, $R^3$, $R^4$ and $R^5$ are as above. $R^1$ is alkyl group having 1 to 2 carbon atoms. $Y^1$ is a halide.

The compound of formula IV can be reduced to the compound of formula V via reaction of step (b). The reaction is carried out utilizing a conventional reducing agent for example alkali metal hydride such as lithium aluminum hydride. The reaction is carried out in a suitable solvent, such as tetrahydrofuran. Any of the conditions conventional in such reduction reactions can be utilized to carry out the reaction of step (b).

The compound of formula V can be converted to the compound of formula VI by displacing hydroxyl group with a halogen group preferred halogen being bromo or chloro. Appropriate halogenating reagents include but are not limited to oxalyl chloride, thionyl chloride, bromine, phosphorous tribromide, carbon tetrabromide and the like. Any conditions conventional in such halogenation reactions can be utilized to carry out the reaction of step (c).

The compound of formula VI can be converted to the compound of formula VII by reacting VI with an alkali metal cyanide for example copper, sodium or potassium cyanide. The reaction is carried out in a suitable solvent, such as N,N-dimethylformamide, ethanol, dimethyl sulfoxide and the like. Any of the conditions conventionally used in the preparation of nitrile can be utilized to carry out the reaction of step (d).

The compound of formula VII can be converted to the compound of formula VIII via reaction step (e) by acid or base hydrolysis. In carrying out this reaction, it is generally preferred to utilize basic hydrolysis, for example aqueous sodium hydroxide. Any of the conditions conventionally used in hydrolysis of nitrile can be utilized to carry out the reaction of step (e). The conventional techniques such as extraction, evaporation, chromatography and recrystallization can be utilized to purify the product.

The compound of formula VIII is the compound of formula I where m is 1 and $R^1$ is H. The compound of formula VIII can be converted to the compound of formula I where $R^1$ is alkyl having 1 to 2 carbon atoms by esterification of compound of formula VIII with methanol or ethanol. The reaction can be carried out either by using catalysts for example $H_2SO_4$, TsOH and the like or by using dehydrating agents for example dicyclohexylcarbodiimide and the like. Any of the conditions conventional in such esterification reactions can be utilized to carry out the reaction.

The compound of formula VI can be reacted with diethyl malonate utilizing a suitable base for example sodium hydride to give the compound of formula IX. The reaction is carried out in suitable solvent, such as dimethylformamide, tetrahydrofuran and the like. Any of the conditions conventional in such alkylation reactions can be utilized to carry out the reaction of step (f).

The compound of formula IX can be hydrolyzed and decarboxylated utilizing sodium hydroxide in suitable solvent, such as ethanol-water to give the compound of formula X. Any of the conditions conventional in such reactions can be utilized to carry out the reaction of step (g). The conventional techniques such as extraction, evaporation, chromatography and recrystallization can be utilized to purify the product.

The compound of formula X is the compound of formula I where m is 2 and $R^1$ is H. The compound of formula X can be converted to the compound of formula I where $R^1$ is alkyl having 1 to 2 carbon atoms by esterification of the compound of formula X with methanol or ethanol. The reaction can be carried out either by using catalysts for example $H_2SO_4$, TsOH and the like or by using dehydrating agents for example dicyclohexylcarbodiimide and the like. Any of the conditions conventional in such esterification reactions can be utilized to carry out the reaction.

The compound of formula X can be reduced to give the compound of formula XI via reaction of step (h). This reaction can be carried out in the same manner as described hereinbefore in the reaction of step (b).

The compound of formula XI can be converted to the compound of formula XII via reaction of step (i) in the same manner as described hereinbefore in connection with the reaction of step (c).

The compound of formula XII can be converted to the compound of formula XIII via reaction of step (j) in the same manner as described hereinbefore in connection with the reaction of step (d).

The compound of formula XIII can be converted to the compound of formula XIV via reaction of step (k) in the same manner as described hereinbefore in connection with the reaction of step (e). The conventional techniques such as extraction, evaporation, chromatography and recrystallization can be utilized to purify the product.

The compound of formula XIV is the compound of formula I where m is 3 and $R^1$ is H. The compound of formula XIV can be converted to the compound of formula I where $R^1$ is alkyl having 1 to 2 carbon atoms by esterification of compound of formula XIV with methanol or ethanol. The reaction can be carried out either by using catalysts for example H$_2$SO$_4$, TsOH and the like or by using dehydrating agents for example dicyclohexylcarbodiimide and the like. Any of the conditions conventional in such esterification reactions can be utilized to carry out the reaction.

The compound of formula XII can be converted to the compound of formula XV via reaction of step (l) in the same manner as described hereinbefore in connection with the reaction of step (f).

The compound of formula XV can be converted to the compound of formula XVI via reaction of step (m) in the same manner as described hereinbefore in connection with the reaction of step (g). The conventional techniques such as extraction, evaporation, chromatography and recrystallization can be utilized to purify the product.

The compound of formula XVI is the compound of formula I where m is 4 and R$^1$ is H. The compound of formula XVI can be converted to the compound of formula I where R$^1$ is alkyl having 1 to 2 carbon atoms by esterification of compound of formula XVI with methanol or ethanol. The reaction can be carried out either by using catalysts for example H$_2$SO$_4$, TsOH and the like or by using dehydrating agents for example dicyclohexylcarbodiimide and the like. Any of the conditions conventional in such esterification reactions can be utilized to carry out the reaction.

If A is phenyl substituted by 1 or 2 groups of hydroxyl, it is generally preferred to protect the hydroxyl group of the compound of formula IV. The suitable protecting group can be described in the Protective Groups in Organic Synthesis by T. Greene.

The protecting group can be deprotected utilizing suitable deprotecting reagents such as those described in Protective Groups in Organic Synthesis by T. Greene.

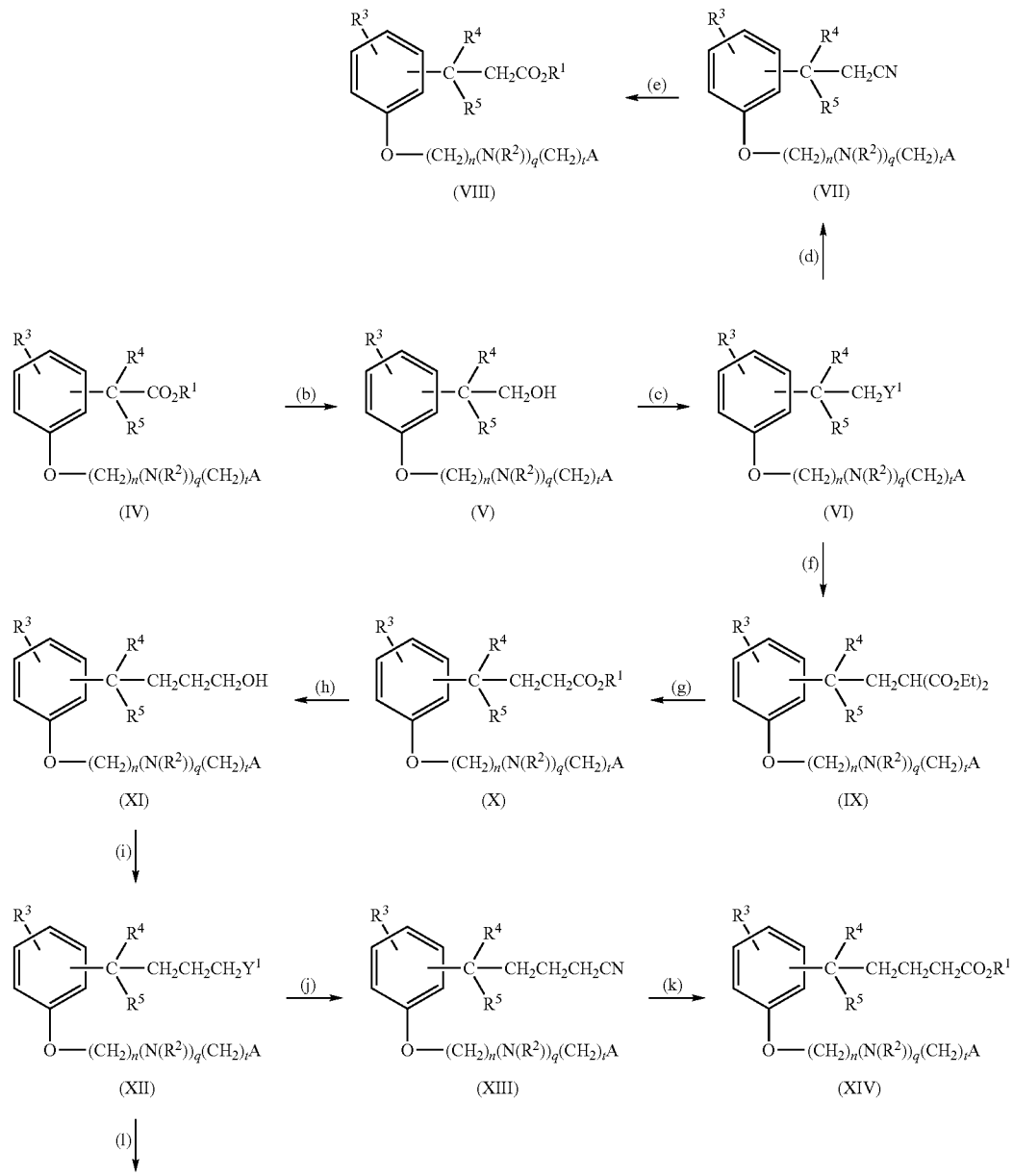

Reaction Scheme 2

-continued

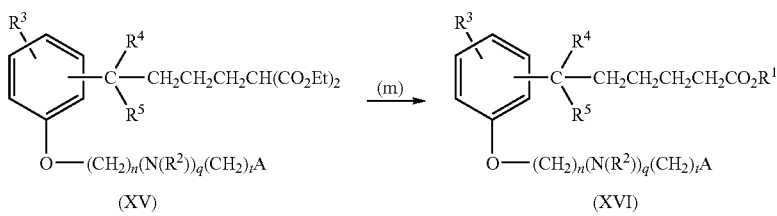

The compound of formula I where x is 2 to 4, m is 0, q is 0 or 1, t is 0 or 1, and n is 1 or 2, $R^2$ is alkyl having from 1 to 3 carbon atoms, $R^3$ is hydrogen, halo, alkoxy having from 1 to 3 carbon atoms or alkyl having from 1 to 3 carbon atoms, $R^4$ and $R^5$ is alkyl having 1 to 3 carbon atoms and the other is hydrogen or alkyl having 1 to 3 carbon atoms. $R^1$ is hydrogen or alkyl having from 1 to 2 carbon atoms, i.e. compounds of formula:

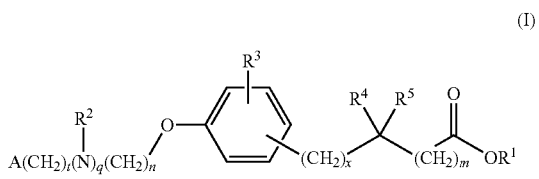

wherein A is described as above, can be prepared via reaction scheme of Scheme 3

In the reaction scheme of Scheme 3, A, t, n, m, q, x, $R^2$, $R^3$, $R^4$ and $R^5$ are as above. Y is a halide or leaving group, p is 2 to 4, s is 1 to 3, u is 1 to 3 and $Y^1$ is halide. $R^1$ is alkyl group having 1 or 2 carbon atoms.

The compound of formula XVII is converted to the compound of formula XIX via reaction of step (n) by Mitsunobu condensation of XVII with XVIII using triphenylphosphine and diethyl azodicarboxylate or diisopropyl azodicarboxylate. The reaction is carried out in a suitable solvent for example tetrahydrofuran. Any of the conditions conventionally used in Mitsunobu reactions can be utilized to carry out the reaction of step (n).

The compound of formula XIX can also be prepared by etherifying or alkylating the compound of formula XVII with the compound of formula XX or with the compound of formula XXI via the reaction of step (o) by using suitable base such as potassium carbonate, sodium hydride, triethylamine, pyridine and the like. In the compound of formula XXI, Y, include but are not limited to mesyloxy, tosyloxy, chloro, bromo, iodo, and the like. Any conventional conditions to alkylate a hydroxyl group with a halide or leaving group can be utilized to carry out the reaction of step (o). The reaction of step (o) is preferred over step (n) if the compound of formula XXI is readily available.

The compound of formula XIX is converted to the compound of formula XXIII via reaction of step (p) using Wittig reaction by treating the compound of formula XIX with the compound of formula XXII. Any conventional method of reacting an aldehyde with triarylphosphine hydrohalide can be utilized to carry out the reaction of step (p). Any of the conditions conventional in Wittig reactions can be utilized to carry out the reaction of step (p). The product can be isolated and purified by techniques such as extraction, evaporation, chromatography, and recrystallization.

The compound of formula XXIII is converted to the compound of formula XXIV via reaction of step (q) by hydrogenation. The reaction is carried out utilizing chlorotris(triphenylphosphine)rhodium (Wilkinson's catalyst). The reaction is carried out in a suitable solvent for example absolute ethanol and the like. Any of the conditions conventional in such reactions can be utilized to carry out the reaction of step (q). The product can be isolated and purified by techniques such as extraction, evaporation, chromatography, and recrystallization.

The compound of formula XXIV is alkylated with the compound of formula III via reaction of step (r) to produce the compound of formula XXV. The reaction is carried out in a suitable solvent, such as tetrahydrofuran, tetrahydrofuran/1,3-dimethyl-3,4,5,6-tetrahydro-2(1H)-pyrimidinone, terahydrofuran/hexamethylphosphoramide and the like. Generally, the reaction is carried out in the presence of 2 to 3 molar equivalents of base to produce the compound of formula XXV where $R^4$ is alkyl having 1 to 3 carbon atoms and $R^5$ is hydrogen or 4 to 6 molar equivalents of base to produce the compound of formula XXV where $R^4$ and $R^5$ is alkyl having 1 to 3 carbon atoms. The conventional base for this purpose can be sodium hydride, potassium hydride, potassium bis(trimethylsilyl)amide, lithium bis(trimethylsilyl)amide, lithium diisopropylamide and the like. In carrying out this reaction it is generally preferred to utilize alkali metal salts of hexamethyldisilane. The reaction is carried out at temperatures from −78° C. to 25° C. Generally, the reaction requires 6 to 72 hours. The conventional techniques such as extraction, evaporation, chromatography and recrystallization can be utilized to purify the product.

The compound of formula XXV is the compound of formula I where $R^1$ is alkyl group having from 1 to 2 carbon atoms. The compound of formula XXV can be converted to the free acid i.e. the compound of formula I where $R^1$ is H by ester hydrolysis. Any conventional method of ester hydrolysis will produce the compound of formula I where $R^1$ is H.

If A is phenyl substituted by 1 or 2 groups of hydroxyl, it is generally preferred to protect the hydroxyl group of the compound of formula XVI, the compound of formula XX and the compound of formula XXI. The suitable protecting group can be described in the Protective Groups in Organic Synthesis by T. Greene.

The protecting group can be deprotected utilizing suitable deprotecting reagents such as those described in Protective Groups in Organic Synthesis by T. Greene.

Reaction Scheme 3

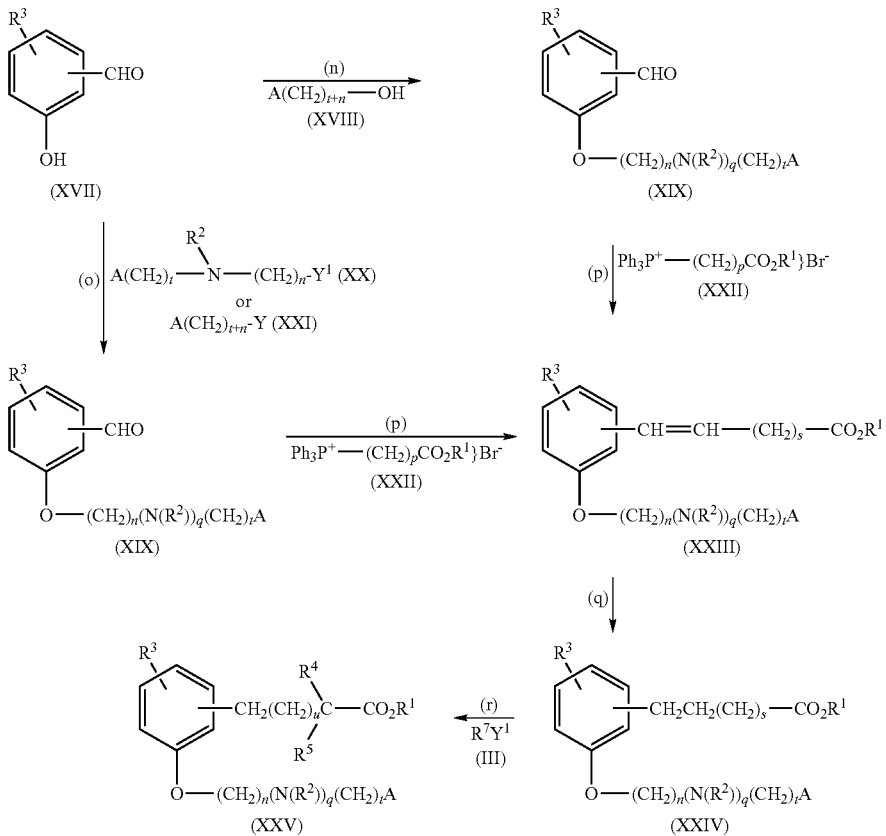

The compound of formula II where m is 0, x is 0, q is 0, t is 0 or 1, and n is 1 or 2, $R^3$ is hydrogen, halo, alkoxy having from 1 to 3 carbon atoms or alkyl having from 1 to 3 carbon atoms, and $R^1$ is alkyl having from 1 to 2 carbon atoms, i.e. compounds of formula:

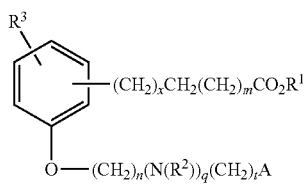

wherein A is described as above, can be prepared via reaction scheme of Scheme 4.

In the reaction scheme of Scheme 4, A, t, n, m, q, x, $R^1$ and $R^3$ are as above. Y is halide or leaving group.

The compound of formula XXVI is converted to the compound of formula II via reaction of step (s) using Mitsunobu condensation of XXVI with XVII using triphenylphosphine and diethyl azodicarboxylate or diisopropyl azodicarboxylate. The reaction is carried out in a suitable solvent for example tetrahydrofuran. Any of the conditions conventionally used in Mitsunobu reactions can be utilized to carry out the reaction of step (s).

The compound of formula II can also be prepared by etherifying or alkylating the compound of formula XXVI with the compound of formula XXI via reaction of step (s). In the compound of formula XXI, Y, include but are not limited to mesyloxy, tosyloxy, chloro, bromo, iodo, and the like. Any conventional method of etherifying of a hydroxyl group by reaction with a halide or leaving group can be utilized to carry out the reaction of step (s).

Reaction Scheme 4

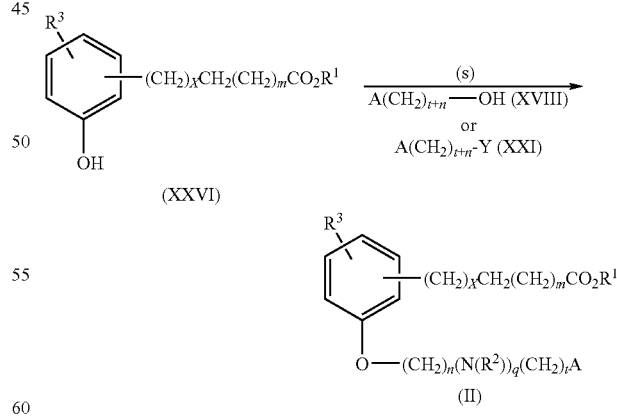

The compound of formula II where m is 0, x is 0, q is 1, t is 0 or 1, and n is 1 or 2, $R^2$ is alkyl having from 1 to 3 carbon atoms, $R^3$ is hydrogen, halo, alkoxy having from 1 to 3 carbon atoms or alkyl having from 1 to 3 carbon atoms, and $R^1$ is alkyl having from 1 to 2 carbon atoms, i.e. compounds of formula:

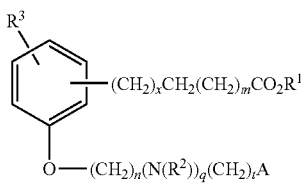

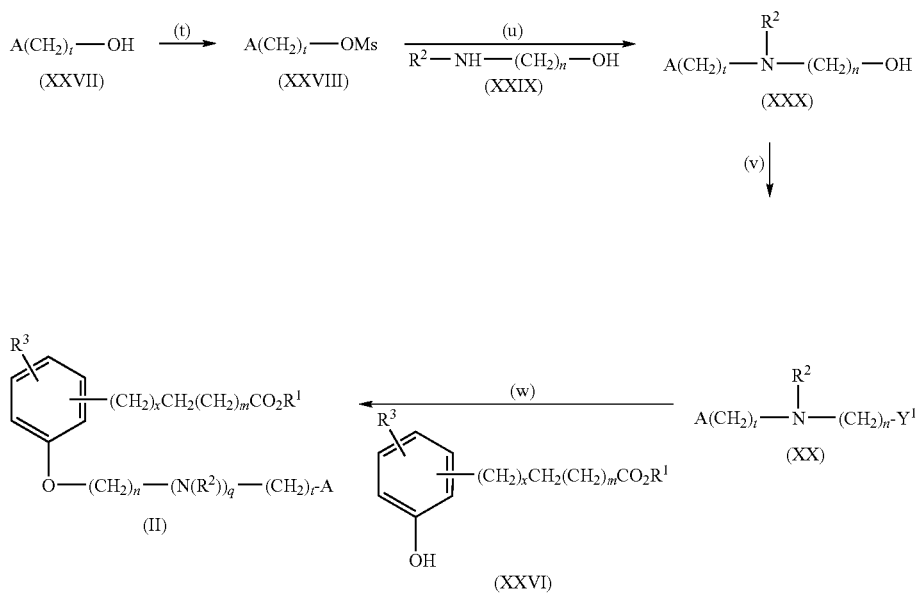

wherein A is described as above, can be prepared via the reaction scheme of Scheme 5.

In the reaction scheme of Scheme 5, A, t, m, n, q, x, $R^1$, $R^2$, and $R^3$ are as above. $Y^1$ is halide.

The compound of formula XXVII can be mesylated to furnish the compound of formula XXVIII via the reaction of step (t). Any conventional conditions to carry out the mesylation reaction of a hydroxyl group can be utilized to carry out the step (t). The compound of formula XXVIII is then heated with the compound of formula XXIX to produce the compound of formula XXX. Any of the conditions conventional to produce amino alcohols can be utilized to carry out the reaction of step (u).

In the compound of formula XXX, alcohol can be displaced by chloro or bromo by treating the compound of formula XXX with oxalyl chloride, thionyl chloride, bromine, phosphorus tribromide and the like to produce the compound of formula XX. Any conventional method to displace alcohol with chloro or bromo can be utilized to carry out the reaction of step (v).

The compound of formula XX can be reacted with the compound of formula XXVI via reaction of step (w) in the presence of a suitable base such as potassium carbonate, sodium hydride, triethylamine, pyridine and the like. The reaction is carried out in conventional solvent such as N,N-dimethylformamide, tetrahydrofuran, dichloromethane and the like to produce the corresponding compound of formula II. Any conventional method of etherification of a hydroxyl group in the presence of base (preferred base being potassium carbonate) with chloro or bromo can be utilized to carry out the reaction of step (w).

If A is phenyl substituted by 1 or 2 groups of hydroxyl, it is generally preferred to protect the hydroxyl group. The suitable protecting group can be described in the Protective Groups in Organic Synthesis by T. Greene.

The protecting group can be deprotected utilizing suitable deprotecting reagents such as those described in Protective Groups in Organic Synthesis by T. Greene.

The compound of formula XXVI where m is 0, x is 0, $R^3$ is hydrogen, halo, alkoxy having from 1 to 3 carbon atoms or alkyl having from 1 to 3 carbon atoms, and $R^1$ is alkyl having from 1 to 2 carbon atoms, i.e. compounds of formula:

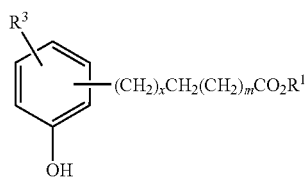

can be prepared via the reaction scheme of Scheme 6.

In the reaction scheme of Scheme 6, $R^1$ and $R^3$ are described as above. $Y^1$ is a halide.

The compound of formula XXXI can be reduced to give the compound of formula XXXII via reaction of step (x). The reaction is carried out utilizing a conventional reducing agent for example alkali metal hydride such as lithium aluminum hydride. The reaction is carried out in a suitable solvent, such as tetrahydrofuran and the like. Any of the conditions conventional in such reduction reactions can be utilized to carry out the reaction of step (x).

The compound of formula XXXII can be converted to the compound of formula XXXIII by displacing hydroxyl group with a halogen group preferred halogen being bromo or chloro. Appropriate halogenating reagents include but are not limited to oxalyl chloride, thionyl chloride, bromine, phosphorous tribromide, carbon tetrabromide and the like. Any conditions conventional in such halogenation reactions can be utilized to carry out the reaction of step (y).

The compound of formula XXXIII can be converted to the compound of formula XXXIV by reacting XXXIII with metal cyanide for example copper, sodium or potassium cyanide. The reaction is carried out in a suitable solvent, such as N,N-dimethylformamide, ethanol, dimethyl sulfoxide and the like. Any of the conditions conventionally used in the preparation of nitrile can be utilized to carry out the reaction of step (z).

The compound of formula XXXIV can be converted to the compound of formula XXXV via reaction of step (a') by acid or base hydrolysis. In carrying out this reaction, it is generally preferred to utilize basic hydrolysis, for example aqueous sodium hydroxide. Any of the conditions conventionally used in hydrolysis of nitrites can be utilized to carry out the reaction of step (a').

The compound of formula XXXV can be converted to compound of formula XXVI by esterification of compound of formula XXXV with methanol or ethanol. The reaction can be carried out either by using catalyst for example $H_2SO_4$, TsOH and the like or by using dehydrating agent for example dicyclohexylcarbodiimide and the like. Any of the conditions conventional in such esterification reactions can be utilized to carry out the reaction of step (b').

as tetrahydrofuran. Any of the conditions conventional in such reduction reactions can be utilized to carry out the reaction of step (c').

The compound of formula XXXVII is the compound of formula XVIII where t is 0 and n is 1.

The compound of formula XXXVII can be converted to the compound of formula XXXVIII by displacing hydroxyl group with a halogen group preferred halogen being bromo or chloro. Appropriate halogenating reagents include but are not limited to oxalyl chloride, thionyl chloride, bromine, phosphorous tribromide, carbon tetrabromide and the like. Any conditions conventional in such halogenation reactions can be utilized to carry out the reaction of step (d').

The compound of formula XXXVIII is the compound of formula XXI where t is 0 and n is 1.

The compound of formula XXXVIII can be converted to the compound of formula XXXIX by reacting XXXVIII with metal cyanide for example copper, sodium or potassium cyanide. The reaction is carried out in a suitable solvent, such as ethanol, dimethyl sulfoxide and N,N-dimethylformamide and the like. Any of the conditions conventionally used in the preparation of nitrites can be utilized to carry out the reaction of step (e').

The compound of formula XXXIX can be converted to the compound of formula XL via reaction step (f') by acid or base hydrolysis. In carrying out this reaction it is generally preferred to utilize basic hydrolysis, for example aqueous

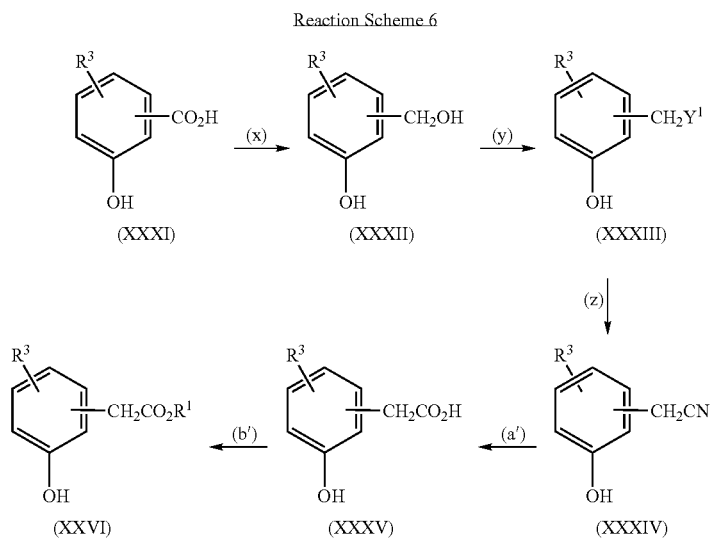

Reaction Scheme 6

The compound of formula XVIII, where t is 0 or 1, n is 1 or 2, i.e. compounds of formula:

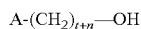

and compound of formula XXI, where t is 0 or 1, n is 1 or 2, i.e. compounds of formula:

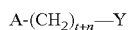

can be prepared via reaction scheme of Scheme 7.

In the reaction of Scheme 7, A is described as above. Y is a leaving group.

The compound of formula XXXVI can be reduced to the compound of formula XXXVII via reaction of step (c'). The reaction is carried out utilizing a conventional reducing agent for example alkali metal hydride such as lithium aluminum hydride. The reaction is carried out in a suitable solvent, such sodium hydroxide. Any of the conditions conventionally used in hydrolysis of nitriles can be utilized to carry out the reaction of step (f').

The compound of formula XL can be reduced to give the compound of formula XLI via reaction of step (g'). This reaction can be carried out in the same manner as described hereinbefore in the reaction of step (c').

The compound of formula XLI is the compound of formula XVIII where t is 1 and n is 1. The compound of formula XLI can be converted to the compound of formula XLII via reaction of step (h') in the same manner as described hereinbefore in connection with the reaction of step (d').

The compound of formula XLII is the compound of formula XXI where t is 1 and n is 1. The compound of formula XXXVIII can be reacted with diethyl malonate utilizing a suitable base for example sodium hydride to give compound of formula XLIII. The reaction is carried out in suitable solvents, such as N,N-dimethylformamide, tetrahydrofuran and the like. Any of the conditions conventional in such alkylation reactions can be utilized to carry out the reaction of step (i').

The compound of formula XLIII can be hydrolyzed and decarboxylated utilizing sodium hydroxide in suitable solvent, such as ethanol-water to give the compound of formula XLIV. Any of the conditions conventional in such reactions can be utilized to carry out the reaction of step (j').

The compound of formula XLIV can be converted to the compound of formula XLV via reaction of step (k') in the same manner as described hereinbefore in connection with the reaction of step (c').

The compound of formula XLV is the compound of formula XVIII where t is 1 and n is 2.

The compound of formula XLV can be converted to the compound of formula XLVI via reaction of step (l') in the same manner as described hereinbefore in connection with the reaction of step (d').

The compound of formula XLVI is the compound of formula XXI where t is 1 and n is 2. If A is phenyl substituted by 1 or 2 groups of hydroxyl, it is generally preferred to protect the hydroxyl group of the formula XXXVI. The suitable protecting group can be described in the Protective Groups in Organic Synthesis by T. Greene.

The protecting group can be deprotected utilizing suitable deprotecting reagents such as those described in Protective Groups in Organic Synthesis by T. Greene.

4. 2-Br-3-OHC$_6$H$_3$CO$_2$H
WO 9628423.
5. 4-Br-3-OHC$_6$H$_3$CO$_2$H
WO 2001002388.
6. 3-Br-5-OHC$_6$H$_3$CO$_2$H
Journal of labelled Compounds and Radiopharmaceuticals (1992), 31 (3), 175-82.
7. 2-Br-5-OHC$_6$H$_3$CO$_2$H and 3-Cl-4-OHC$_6$H$_3$CO$_2$H
WO 9405153 and U.S. Pat. No. 5,519,133.
8. 2-Br-4-OHC$_6$H$_3$CO$_2$H and 3-Br-4-OHC$_6$H$_3$CO$_2$H
WO 20022018323
9. 2-Cl-6-OHC$_6$H$_3$CO$_2$H
JP 06293700
10. 2-Cl-3-OHC$_6$H$_3$CO$_2$H
Proceedings of the Indiana Academy of Science (1983), Volume date 1982, 92, 145-51.
11. 3-Cl-5-OHC$_6$H$_3$CO$_2$H
WO 2002000633 and WO 2002044145.
12. 2-Cl-5-OHC$_6$H$_3$CO$_2$H
WO 9745400.
13. 5-I-2-OHC$_6$H$_3$CO$_2$H and 3-I, 2-OHC$_6$H$_3$CO$_2$H
Z. Chem. (1976), 16(8), 319-320.
14. 4-I-2-OHC$_6$H$_3$CO$_2$H
Journal of Chemical Research, Synopses (1994), (11), 405.
15. 6-I-2-OHC$_6$H$_3$CO$_2$H
U.S. Pat. No. 4,932,999.
16. 2-I-3-OHC$_6$H$_3$CO$_2$H and 4-I-3-OHC$_6$H$_3$CO$_2$H
WO 9912928.

Reaction Scheme 7

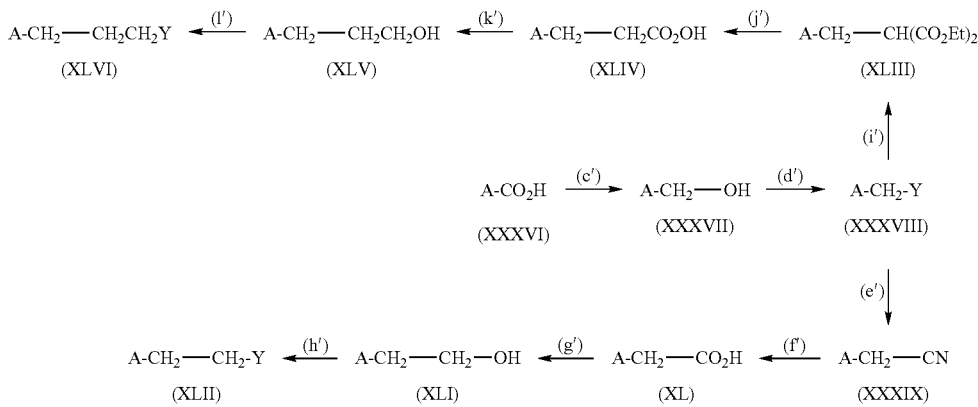

The compound of formula XXXI, where R$^3$ is halo, i.e. compounds of formula:

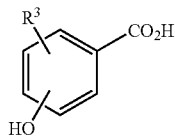

are either commercially available or can be prepared according to the methods described in the literature as follows:
1. 3-Br or F-2-OHC$_6$H$_3$CO$_2$H
Canadian Journal of Chemistry (2001), 79(11) 1541-1545.
2. 4-Br-2-OHC$_6$H$_3$CO$_2$H
WO 9916747 or JP 04154773.
3. 2-Br-6-OHC$_6$H$_3$CO$_2$H
JP 47039101.

17. 5-I-3-OHC$_6$H$_3$CO$_2$H
J. Med. Chem. (1973), 16(6), 684-7.
18. 2-I-4-OHC$_6$H$_3$CO$_2$H
Collection of Czechoslovak Chemical Communications, (1991), 56(2), 459-77.
19. 3-I-4-OHC$_6$H$_3$CO$_2$,
J.O.C. (1990), 55(18), 5287-91.

The compound of formula XXXI, where R$^3$ is alkoxy having from 1 to 3 carbon atoms, i.e. compounds of formula:

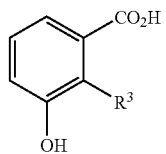

can be prepared via the reaction scheme of Scheme 8.

In the reaction scheme of Scheme 8, $R^1$ and $R^3$ are as above. $R^6$ is alkyl group having from 1 to 2 carbon atoms. $R^8$ is alkyl having from 1 to 3 carbon atoms. $Y^1$ is a halide.

The compound of formula XLVII can be converted to the compound of formula XLVIII by reducing aldehyde to primary alcohol. In carrying out this reaction, it is preferred but not limited to use sodium borohydride as the reducing reagent. Any of the conditions suitable in such reduction reactions can be utilized to carry out the reaction of step (m'). The compound of formula XLVIII can be converted to the compound of formula XLIX via reaction of step (n') by protecting 1-3 Diols by using 1,1,3,3-Tetraisopropyldisiloxane. The suitable conditions for this protecting group can be described in the Protecting Groups in Organic Synthesis by T. Greene.

The compound of formula XLIX can be converted to the compound of formula L via reaction of step (o') by protecting phenol group by using benzyl bromide. The suitable conditions for this protecting group can be described in the Protecting Groups in Organic Synthesis by T. Greene.

The compound of formula L can be converted to the compound of formula LI by deprotection using tetrabutylammonium fluoride via reaction of step (p'). The suitable conditions for the deprotection can be described in the Protecting Groups in Organic Synthesis by T. Greene.

The compound of formula LI can be converted to compound of formula LII via reaction of step (q') by oxidation. Any conventional oxidizing group that converts primary alcohol to an acid for example chromium oxide and the like can be utilized to carry out the reaction of step (q').

The compound of formula LII can be converted to the compound of formula LIII by esterification of compound of formula LII with methanol or ethanol. The reaction can be carried out either by using catalyst for example $H_2SO_4$, TsOH and the like or by using dehydrating agent for example dicyclohexylcarbodiimide and the like. Any of the conditions conventional in such esterification reactions can be utilized to carry out the reaction of step (r').

The compound of formula LIII can be converted to the compound of formula LVI via reaction of step (s') using Mitsunobu condensation of LIII with LIV using triphenylphosphine and diethyl azodicarboxylate or diisopropyl azodicarboxylate. The reaction can be carried out in a suitable solvent for example tetrahydrofuran. Any of the conditions conventionally used in Mitsunobu reactions can be utilized to carry out the reaction of step (s').

The compound of formula LIII can also be converted to the compound of formula LVI by etherifying or alkylating the compound of formula LIII with the compound of formula LV as in reaction of step (s'). The reaction is carried out by utilizing a suitable base such as potassium carbonate, sodium hydride, triethylamine, pyridine and the like. The reaction is carried out in a conventional solvent such as N,N-dimethylformamide, tetrahydrofuran, dichloromethane and the like. Any conventional method of etherification of a hydroxyl group in the presence of base (preferred base being potassium carbonate) with chloro or bromo can be utilized to carry out the reaction of step (s').

The compound of formula LVI can be converted to the compound of formula XXXI by deprotection of ester and benzyl groups via reaction of steps (t'). The suitable deprotecting reagents can be described in the Protecting Groups in Organic Synthesis by T. Greene.

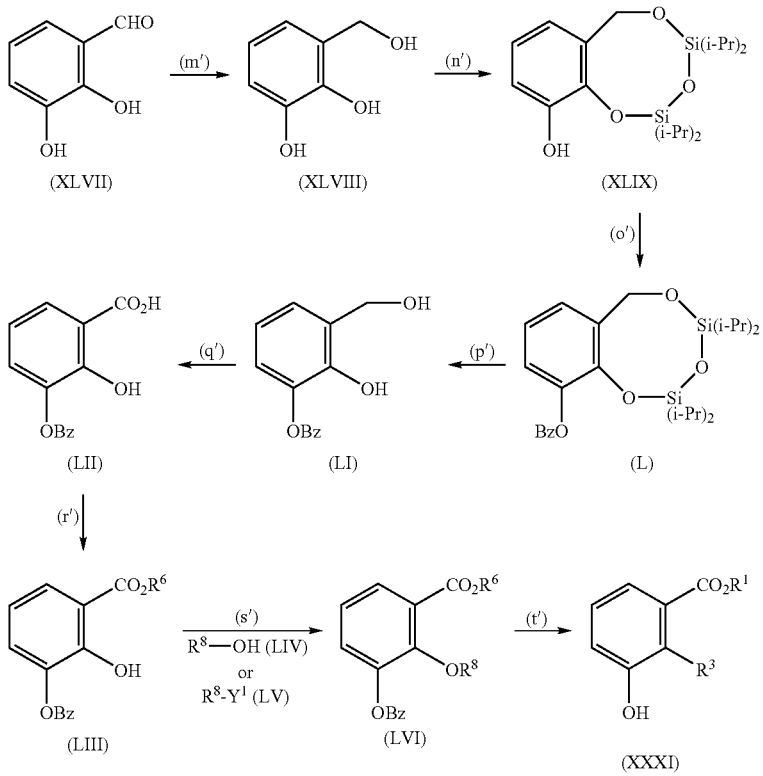

Reaction Scheme 8

The compound of formula XXXI, where $R^3$ is alkoxy having from 1 to 3 carbon atoms, i.e. compounds of formula:

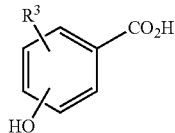

are either commercially available or can be prepared according to the methods described in the literature as follows:
1. 2-OMe-4-OHC$_6$H$_3$CO$_2$H
US 2001034343 or WO 9725992.
2. 5-OMe-3-OHC$_6$H$_3$CO$_2$H
J.O.C (2001), 66(23), 7883-88.
3. 2-OMe-5-OHC$_6$H$_3$CO$_2$H
U.S. Pat. No. 6,194,406 (Page 96) and Journal of the American Chemical Society (1985), 107(8), 2571-3.
4. 3-OEt-5-OHC$_6$H$_3$CO$_2$H
Taiwan Kexue (1996), 49(1), 51-56.
5. 4-OEt-3-OHC$_6$H$_3$CO$_2$H
WO 9626176
6. 2-OEt-4-OHC$_6$H$_3$CO$_2$H
Takeda Kenkyusho Nempo (1965), 24, 221-8.
JP 07070025.
7. 3-OEt-4-OHC$_6$H$_3$CO$_2$H
WO 9626176.
8. 3-OPr-2-OHC$_6$H$_3$CO$_2$H
JP 07206658, DE 2749518.
9. 4-OPr-2-OHC$_6$H$_3$CO$_2$H
Farmacia (Bucharest) (1970), 18(8), 461-6.
JP 08119959.
10. 2-OPr-5-OHC$_6$H$_3$CO$_2$H and 2-OEt-5-OHC$_6$H$_3$CO$_2$H
Adapt synthesis from U.S. Pat. No. 6,194,406 (Page 96) by using propyl iodide and ethyl iodide.
11. 4-OPr-3-OHC$_6$H$_3$CO$_2$H
Adapt synthesis from WO 9626176
12. 2-OPr-4-OHC$_6$H$_3$CO$_2$H
Adapt synthesis from Takeda Kenkyusho Nempo (1965), 24, 221-8 by using propyl halide.
13. 4-OEt-3-OHC$_6$H$_3$CO$_2$H
Biomedical Mass Spectrometry (1985), 12(4), 163-9.
14. 3-OPr-5-OHC$_6$H$_3$CO$_2$H
Adapt synthesis from Taiwan Kexue (1996), 49(1), 51-56 by using propyl halide.

The compound of formula XXXI, where $R^3$ is an alkyl having 1 to 3 carbon atoms, i.e. compounds of formula:

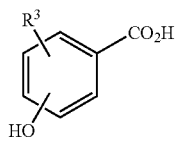

are either commercially available or can be prepared according to the methods described in the literature as follows:
1. 5-Me-3-OHC$_6$H$_3$CO$_2$H and 2-Me-5-OHC$_6$H$_3$CO$_2$H
WO 9619437.
J.O.C. 2001, 66, 7883-88.
2. 2-Me-4-OHC$_6$H$_3$CO$_2$H
WO 8503701.
3. 3-Et-2-OHC$_6$H$_3$CO$_2$H and 5-Et-2-OHC$_6$H$_3$CO$_2$H
J. Med. Chem. (1971), 14(3), 265.
4. 4-Et-2-OHC$_6$H$_3$CO$_2$H
Yaoxue Xuebao (1998), 33(1), 67-71.
5. 2-Et-6-OHC$_6$H$_3$CO$_2$H and 2-n-Pr-6-OHC$_6$H$_3$CO$_2$H
J. Chem. Soc., Perkin Trans 1 (1979), (8), 2069-78.
6. 2-Et-3-OHC$_6$H$_3$CO$_2$H
JP 10087489 and WO 9628423.
7. 4-Et-3-OHC$_6$H$_3$CO$_2$H
J.O.C. 2001, 66, 7883-88.
WO 9504046.
8. 2-Et-5-OHC$_6$H$_3$CO$_2$H
J.A.C.S (1974), 96(7), 2121-9.
9. 2-Et-4-OHC$_6$H$_3$CO$_2$H and 3-Et-4-OHC$_6$H$_3$CO$_2$H
JP 04282345.
10. 3-n-Pr-2-OHC$_6$H$_3$CO$_2$H
J.O.C (1991), 56(14), 4525-29.
11. 4-n-Pr-2-OHC$_6$H$_3$CO$_2$H
EP 279630.
12. 5-n-Pr-2-OHC$_6$H$_3$CO$_2$H
J. Med. Chem (1981), 24(10), 1245-49.
13. 2-n-Pr-3-OHC$_6$H$_3$CO$_2$H
WO 9509843 and WO 9628423.
14. 4-n-Pr-3-OHC$_6$H$_3$CO$_2$H
WO 9504046.
15. 2-n-Pr-5-OHC$_6$H$_3$CO$_2$H
Synthesis can be adapted from J.A.C.S (1974), 96(7), 2121-9 by using ethyl alpha formylvalerate.
16. 3-n-Pr-4-OHC$_6$H$_3$CO$_2$H
Polymer (1991), 32(11) 2096-105.
17. 2-n-Pr-4-OHC$_6$H$_3$CO$_2$H
3-Propylphenol can be methylated to 3-Propylanisole, which was then formylated to 4-Methoxy-3-benzaldehyde. The aldehyde can be oxidized by Jone's reagent to give corresponding acid and deprotection of methyl group by BBr$_3$ will give the title compound.
18. 1. 3-Et-5-OHC$_6$H$_3$CO$_2$H and 3-Pr-n-5-OHC$_6$H$_3$CO$_2$H
Adapt synthesis from J.O.C. 2001, 66, 7883-88 by using 2-Ethylacrolein and 2-Propylacrolein.

The compound of formula XVII where $R^3$ is hydrogen, halo, alkoxy having from 1 to 3 carbon atoms or alkyl having from 1 to 3 carbon atoms, i.e. compounds of formula:

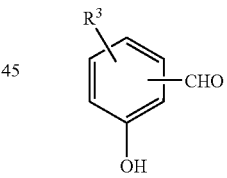

can be prepared via reaction of scheme 9.

In the reaction scheme of Scheme 9, $R^3$ is as above. $R^6$ is alkyl group having from 1 to 2 carbon atoms, and P is a protecting group.

The compound of formula LVII can be converted to the compound of formula LVIII via the reaction of step (u') by protecting the hydroxy group by utilizing suitable protecting group such as those described in Protecting Groups in Organic Synthesis by T. Greene.

The compound of formula LVIII can be converted to the compound of formula LIX via reaction of step (v') by reducing acid to alcohol. The reaction can be carried out utilizing a conventional reducing agent for example alkali metal hydride such as lithium aluminum hydride. The reaction can be carried out in a suitable solvent, such as tetrahydrofuran. Any of the conditions conventional in such reduction reactions can be utilized to carry out the reaction of step (v').

The compound of formula LIX can be converted to the compound of formula LX via reaction of step (w') by oxidation of alcohol to the aldehyde. The reaction can be carried out utilizing a suitable oxidizing agent for example pyridinium chlorochromate, dimethyl sulfoxide activated by 2,4,6-trichloro[1,3,5]-triazine (cyanuric chloride, TCT) under Swern oxidation conditions (J.O.C. 2001, 66, 7907-7909) and the like. Any of the conditions conventional in such oxidation reactions can be utilized to carry out the reaction of step (w').

In the compound of formula LX, the hydroxy group can be deprotected via reaction of step (x') by utilizing suitable deprotecting reagents such as those described in Protecting Groups in Organic Synthesis by T. Greene to give the compound of formula XVII.

Reaction Scheme 9

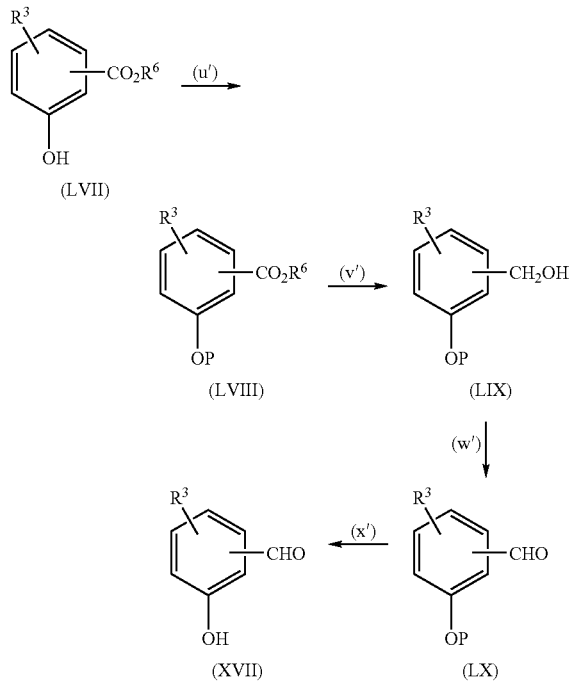

The compound of formula XXII, where $R^1$ is alkyl group having from 1 to 2 carbon atoms and p is 2 to 4, i.e. compounds of formula:

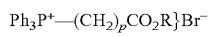

can be prepared via reaction of scheme 10.

In the reaction scheme of Scheme 10, $R^1$ and p are as above.

The compound of formula LXI is reacted with the compound of formula LXII via the reaction of step (y') to give the compound of formula XXII. Any of the conditions conventionally used in reacting triphenylphosphine with hydrohalide can be utilized to carry out the reaction of step (y').

Reaction Scheme 10

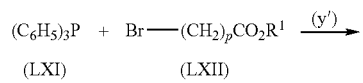

-continued

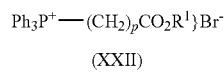

The compound of formula LVII where $R^6$ is alkyl group having from 1 to 2 carbon atoms and $R^3$ is halo, alkoxy having from 1 to 3 carbon atoms or alkyl having from 1 to 3 carbon atoms, i.e. compounds of formula:

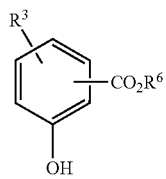

can be prepared via reaction of scheme 11.

In the reaction of Scheme 11, $R^3$ and $R^6$ are as above.

The compound of formula XXXI can be converted to the compound of formula LVII via reaction of step (z') by esterification of compound of formula XXXI with methanol or ethanol. The reaction can be carried out either by using catalysts for example $H_2SO_4$, TsOH and the like or by using dehydrating agents for example dicyclohexylcarbodiimide and the like. Any of the conditions conventional in such esterification reactions can be utilized to carry out the reaction of step (z').

Reaction Scheme 11

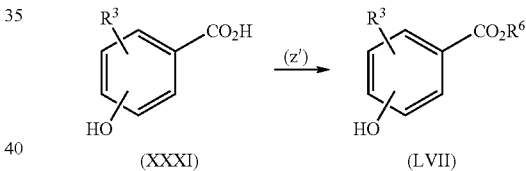

Use in Methods of Treatment

This invention provides a method for treating a mammalian subject with a condition selected from the group consisting of insulin resistance syndrome, diabetes (both primary essential diabetes such as Type I Diabetes or Type II Diabetes and secondary nonessential diabetes) and polycystic ovary syndrome, comprising administering to the subject an amount of a biologically active agent as described herein effective to treat the condition. In accordance with the method of this invention a symptom of diabetes or the chance of developing a symptom of diabetes, such as atherosclerosis, obesity, hypertension, hyperlipidemia, fatty liver disease, nephropathy, neuropathy, retinopathy, foot ulceration and cataracts, each such symptom being associated with diabetes, can be reduced. This invention also provides a method for treating hyperlipidemia comprising administering to the subject an amount of a biologically active agent as described herein effective to treat the condition. As shown in the Examples, compounds reduce serum triglycerides and free fatty acids in hyperlipidemic animals. This invention also provides a method for treating cachexia comprising administering to the subject an amount of a biologically active agent as described herein effective to treat the cachexia. This invention also provides a method for treating obesity comprising administering to the subject an amount of a biologically active agent as described herein effective to treat the condition. This invention also provides a method for treating a condition selected from atherosclerosis or arteriosclerosis comprising administering to the subject an amount of a biologically active agent as described herein effective to treat the condition. The active agents of this invention are effective to treat hyperlipidemia, fatty liver disease, cachexia, obesity, atherosclerosis or arteriosclerosis whether or not the subject has diabetes or insulin resistance syndrome. The agent can be administered by any conventional route of systemic administration. Preferably the agent is administered orally. Accordingly, it is preferred for the medicament to be formulated for oral administration. Other routes of administration that can be used in accordance with this invention include rectally, parenterally, by injection (e.g. intravenous, subcutaneous, intramuscular or intraperitoneal injection), or nasally.

Further embodiments of each of the uses and methods of treatment of this invention comprise administering any one of the embodiments of the biologically active agents described above. In the interest of avoiding unnecessary redundancy, each such agent and group of agents is not being repeated, but they are incorporated into this description of uses and methods of treatment as if they were repeated.

Many of the diseases or disorders that are addressed by the compounds of the invention fall into two broad categories: Insulin resistance syndromes and consequences of chronic hyperglycemia. Dysregulation of fuel metabolism, especially insulin resistance, which can occur in the absence of diabetes (persistent hyperglycemia) per se, is associated with a variety of symptoms, including hyperlipidemia, atherosclerosis, obesity, essential hypertension, fatty liver disease (NASH; non-alcoholic steatohepatitis), and, especially in the context of cancer or systemic inflammatory disease, cachexia. Cachexia can also occur in the context of Type I Diabetes or late-stage Type II Diabetes. By improving tissue fuel metabolism, active agents of the invention are useful for preventing or ameliorating diseases and symptoms associated with insulin resistance, as is demonstrated in animals in the Examples. While a cluster of signs and symptoms associated with insulin resistance may coexist in an individual patient, it many cases only one symptom may dominate, due to individual differences in vulnerability of the many physiological systems affected by insulin resistance. Nonetheless, since insulin resistance is a major contributor to many disease conditions, drugs which address this cellular and molecular defect are useful for prevention or amelioration of virtually any symptom in any organ system that may be due to, or exacerbated by, insulin resistance.

When insulin resistance and concurrent inadequate insulin production by pancreatic islets are sufficiently severe, chronic hyperglycemia occurs, defining the onset of Type II diabetes mellitus (NIDDM). In addition to the metabolic disorders related to insulin resistance indicated above, disease symptoms secondary to hyperglycemia also occur in patients with NIDDM. These include nephropathy, peripheral neuropathy, retinopathy, microvascular disease, ulceration of the extremities, and consequences of nonenzymatic glycosylation of proteins, e.g. damage to collagen and other connective tissues. Attenuation of hyperglycemia reduces the rate of onset and severity of these consequences of diabetes. Because, as is demonstrated in the Examples, active agents and compositions of the invention help to reduce hyperglycemia in diabetes, they are useful for prevention and amelioration of complications of chronic hyperglycemia.

Both human and non-human mammalian subjects can be treated in accordance with the treatment method of this invention. The optimal dose of a particular active agent of the invention for a particular subject can be determined in the clinical setting by a skilled clinician. In the case of oral administration to a human for treatment of disorders related to insulin resistance, diabetes, hyperlipidemia, fatty liver disease, cachexia or obesity the agent is generally administered in a daily dose of from 1 mg to 400 mg, administered once or twice per day. In the case of oral administration to a mouse the agent is generally administered in a daily dose from 1 to 300 mg of the agent per kilogram of body weight. Active agents of the invention are used as monotherapy in diabetes or insulin resistance syndrome, or in combination with one or more other drugs with utility in these types of diseases, e.g. insulin releasing agents, prandial insulin releasers, biguanides, or insulin itself. Such additional drugs are administered in accord with standard clinical practice. In some cases, agents of the invention will improve the efficacy of other classes of drugs, permitting lower (and therefore less toxic) doses of such agents to be administered to patients with satisfactory therapeutic results. Established safe and effective dose ranges in humans for representative compounds are: metformin 500 to 2550 mg/day; glyburide 1.25 to 20 mg/day; GLUCOVANCE (combined formulation of metformin and glyburide) 1.25 to 20 mg/day glyburide and 250 to 2000 mg/day metformin; atorvastatin 10 to 80 mg/day; lovastatin 10 to 80 mg/day; pravastatin 10 to 40 mg/day; and simvastatin 5-80 mg/day; clofibrate 2000 mg/day; gemfibrozil 1200 to 2400 mg/day, rosiglitazone 4 to 8 mg/day; pioglitazone 15 to 45 mg/day; acarbose 75-300 mg/day; repaglinide 0.5 to 16 mg/day.

Type I Diabetes Mellitus: A patient with Type I diabetes manages their disease primarily by self-administration of one to several doses of insulin per day, with frequent monitoring blood glucose to permit appropriate adjustment of the dose and timing of insulin administration. Chronic hyperglycemia leads to complications such as nephropathy, neuropathy, retinopathy, foot ulceration, and early mortality; hypoglycemia due to excessive insulin dosing can cause cognitive dysfunction or unconsciousness. A patient with Type I diabetes is treated with 1 to 400 mg/day of an active agent of this invention, in tablet or capsule form either as a single or a divided dose. The anticipated effect will be a reduction in the dose or frequency of administration of insulin required to maintain blood glucose in a satisfactory range, and a reduced incidence and severity of hypoglycemic episodes. Clinical outcome is monitored by measurement of blood glucose and glycosylated hemoglobin (an index of adequacy of glycemic control integrated over a period of several months), as well as by reduced incidence and severity of typical complications of diabetes. A biologically active agent of this invention can be administered in conjunction with islet transplantation to help maintain the anti-diabetic efficacy of the islet transplant.

Type II Diabetes Mellitus: A typical patient with Type II diabetes (NIDDM) manages their disease by programs of diet and exercise as well as by taking medications such as metformin, glyburide, repaglinide, rosiglitazone, or acarbose, all of which provide some improvement in glycemic control in some patients, but none of which are free of side effects or eventual treatment failure due to disease progression. Islet failure occurs over time in patients with NIDDM, necessitating insulin injections in a large fraction of patients. It is anticipated that daily treatment with an active agent of the invention (with or without additional classes of antidiabetic medication) will improve glycemic control, reduce the rate of islet failure, and reduce the incidence and severity of typical symptoms of diabetes. In addition, active agents of the invention will reduce elevated serum triglycerides and fatty acids, thereby reducing the risk of cardiovascular disease, a major cause of death of diabetic patients. As is the case for all other therapeutic agents for diabetes, dose optimization is done in individual patients according to need, clinical effect, and susceptibility to side effects.

Hyperlipidemia: Elevated triglyceride and free fatty acid levels in blood affect a substantial fraction of the population and are an important risk factor for atherosclerosis and myocardial infarction. Active agents of the invention are useful for reducing circulating triglycerides and free fatty acids in hyperlipidemic patients. Hyperlipidemic patients often also have elevated blood cholesterol levels, which also increase the risk of cardiovascular disease. Cholesterol-lowering drugs such as HMG-CoA reductase inhibitors ("statins") can be administered to hyperlipidemic patients in addition to agents of the invention, optionally incorporated into the same pharmaceutical composition.

Fatty Liver Disease: A substantial fraction of the population is affected by fatty liver disease, also known as nonalcoholic steatohepatitis (NASH); NASH is often associated with obesity and diabetes. Hepatic steatosis, the presence of droplets of triglycerides with hepatocytes, predisposes the liver to chronic inflammation (detected in biopsy samples as infiltration of inflammatory leukocytes), which can lead to fibrosis and cirrhosis. Fatty liver disease is generally detected by observation of elevated serum levels of liver-specific enzymes such as the transaminases ALT and AST, which serve as indices of hepatocyte injury, as well as by presentation of symptoms which include fatigue and pain in the region of the liver, though definitive diagnosis often requires a biopsy. The anticipated benefit is a reduction in liver inflammation and fat content, resulting in attenuation, halting, or reversal of the progression of NASH toward fibrosis and cirrhosis.

Pharmaceutical Compositions

This invention provides a pharmaceutical composition comprising a biologically active agent as described herein and a pharmaceutically acceptable carrier. Further embodiments of the pharmaceutical composition of this invention comprise any one of the embodiments of the biologically active agents described above. In the interest of avoiding unnecessary redundancy, each such agent and group of agents is not being repeated, but they are incorporated into this description of pharmaceutical compositions as if they were repeated.

Preferably the composition is adapted for oral administration, e.g. in the form of a tablet, coated tablet, dragee, hard or soft gelatin capsule, solution, emulsion or suspension. In general the oral composition will comprise from 1 mg to 400 mg of such agent. It is convenient for the subject to swallow one or two tablets, coated tablets, dragees, or gelatin capsules per day. However the composition can also be adapted for administration by any other conventional means of systemic administration including rectally, e.g. in the form of suppositories, parenterally, e.g. in the form of injection solutions, or nasally.

The biologically active compounds can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semil-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances, particularly antidiabetic or hypolipidemic agents that act through mechanisms other than those underlying the effects of the compounds of the invention. Agents which can advantageously be combined with compounds of the invention in a single formulation include but are not limited to biguanides such as metformin, insulin releasing agents such as the sulfonylurea insulin releaser glyburide and other sulfonylurea insulin releasers, cholesterol-lowering drugs such as the "statin" HMG-CoA reductase inhibitors such as atrovastatin, lovastatin, pravastatin and simvastatin, PPAR-alpha agonists such as clofibrate and gemfibrozil, PPAR-gamma agonists such as thiazolidinediones (e.g. rosiglitazone and pioglitazone, alpha-glucosidase inhibitors such as acarbose (which inhibit starch digestion), and prandial insulin releasers such as repaglinide. The amounts of complementary agents combined with compounds of the invention in single formulations are in accord with the doses used in standard clinical practice. Established safe and effective dose ranges for certain representative compounds are set forth above.

The invention will be better understood by reference to the following examples which illustrate but do not limit the invention described herein.

CHEMICAL SYNTHESIS EXAMPLES

Example 1

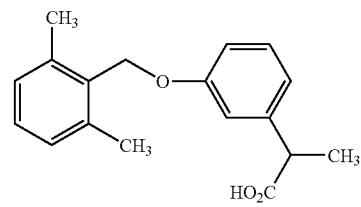

2-(3-(2,6-Dimethylbenzyloxy)phenyl)-2-methylacetic Acid

Step A: Preparation of Ethyl 3-hydroxyphenylacetate

A solution of 3-Hydroxyphenylacetic acid (25 g, 164.31 mmol) and p-Toluenesulfonic acid monohydrate (3.49 g, 18.3 mmol) in abs ethanol (250 ml) was refluxed for 4 hours or until all the starting material is consumed. The reaction mixture was concentrated, diluted with ethyl acetate and washed with water. The organic layer was dried over $Na_2SO_4$, filtered, concentrated, and purified by flash chromatography on a silica gel column (hex:ethyl acetate 2:1) to give the title compound.

$^1$H NMR (270 MHz, $CDCl_3$): 1.2 (t, 3H); 3.5 (s, 2H); 4.1 (q, 2H); 6.6-7.2 (m, 4H).

Step B: Preparation of Ethyl 3-(2,6-dimethylbenzyloxy)phenylacetate

A solution of 2,6-Dimethylbenzyl alcohol (5.25 g, 38.6 mmol) and diisopropyl azodicarboxylate (DIAD, 8.49 g, 42 mmol) in THF (30 ml) and DMF (13 ml) was added drop wise to a solution of Ethyl 3-hydroxyphenylacetate (Step A, 6.66 g, 37 mmol) and triphenylphosphine (11 g, 42 mmol) in THF (100 ml). The reaction mixture was stirred at room temperature for 4 hours, diluted with ether and washed with water. The organic layer was dried over $Na_2SO_4$, filtered, concentrated, and purified by flash chromatography on a silica gel column (hex:ethyl acetate 4:1) to give the title compound.
$^1$H NMR (270 MHz, $CDCl_3$): 1.2 (t, 3H); 2.4 (s, 6H); 3.5 (s, 2H); 4.1 (q, 2H); 5.1 (s, 2H); 6.9 (m, 2H); 7.15-7.35 (m, 5H).

Step C: Preparation of Ethyl 2-(3-(2,6-dimethylbenzyloxy)phenyl)-2-methylacetate To a stirred solution of Ethyl 3-(2,6-dimethylbenzyloxy)phenylacetate (Step B, 4 g, 13.6 mmol) in dry THF (30 ml) at −68° C. under a dry argon atmosphere was added LiHMDS drop wise (1 M solution in THF, 17.45 ml, 17.4 mmol), and the resulting orange solution was stirred at low temperature for 30 minutes before $CH_3I$ (5.71 g, 40.26 mmol) was added. The reaction mixture was slowly warmed to room temperature and stirred for 15 hours. The reaction was quenched with ice, and the product was extracted with EtOAc (2×), the organic phase washed with brine, dried over $Na_2SO_4$, filtered, concentrated and purified by flash chromatography on a silica gel column (hex:ether 5:1) to give the title compound.
$^1$H NMR (270 MHz, $CDCl_3$): 1.2 (t, 3H); 1.5 (t, 3H); 2.4 (s, 6H); 3.7 (m, 1H); 4.1 (q, 2H); 5.0 (s, 2H); 6.9 (m, 2H); 7.15-7.35 (m, 5H).

Step D: Preparation of 2-(3-(2,6-Dimethylbenzyloxy)phenyl)-2-methylacetic Acid

To a stirred solution of Ethyl 2-(3-(2,6-dimethylbenzyloxy)phenyl)-2-methylacetate (Step C, 3 g, 9.6 mmol) in absolute ethanol (60 ml) was added 1N NaOH (20 ml) at room temperature. The reaction mixture was stirred for 3 hours, acidified to pH 3.5-4.0 by 1N HCl, and concentrated. The residue was taken into chloroform and washed with 0.1N HCl, brine, dried over $Na_2SO_4$, filtered, concentrated and purified by flash chromatography on a silica gel column (chloroform:methanol 95:5 spiked with acetic acid) to give the title compound.
$^1$H NMR (270 MHz, $CDCl_3$): 1.5 (t, 3H); 2.4 (s, 6H); 3.7 (m, 1H); 5.0 (s, 2H); 6.9 (m, 2H); 7.15-7.35 (m, 5H).

Example 2

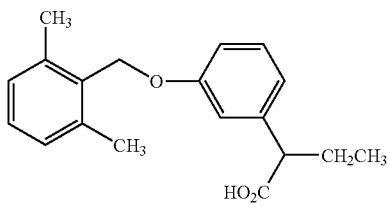

2-(3-(2,6-Dimethylbenzyloxy)phenyl)-2-ethylacetic Acid

Step A: Preparation of Ethyl 3-hydroxyphenylacetate

Using the method of Example 1, Step A, the title compound was obtained.
$^1$H NMR (270 MHz, $CDCl_3$): 1.2 (t, 3H); 3.5 (s, 2H); 4.1 (q, 2H); 6.6-7.2 (m, 4H).

Step B: Preparation of Ethyl 3-(2,6-dimethylbenzyloxy)phenylacetate

Using the method of Example 1, Step B, the title compound was obtained.
$^1$H NMR (270 MHz, $CDCl_3$): 1.2 (t, 3H); 2.4 (s, 6H); 3.5 (s, 2H); 4.1 (q, 2H); 5.1 (s, 2H); 6.9 (m, 2H); 7.15-7.35 (m, 5H).

Step C: Preparation of Ethyl 2-(3-(2,6-dimethylbenzyloxy)phenyl)-2-ethylacetate

To a stirred solution of Ethyl 3-(2,6-dimethylbenzyloxy)phenylacetate (Step B, 4.84 g, 16.2 mmol) in dry THF (60 ml) and HMPA (15 ml) at −78° C. under a dry argon atmosphere was added LDA drop wise (2 M solution in THF, 25 ml, 48.72 mmol), and the resulting orange solution was stirred at low temperature for 30 minutes before $CH_3CH_2I$ (10.13 g, 64.96 mmol) was added. The reaction mixture was slowly warmed to room temperature and stirred for 15 hours. The reaction was quenched with aqueous citric acid, and the product was extracted with EtOAc (2×), the organic phase washed with brine, dried over $Na_2SO_4$, filtered, concentrated and purified by flash chromatography on a silica gel column (hex:ethyl acetate 4:1) to give the title compound.
$^1$H NMR (270 MHz, $CDCl_3$): 0.9 (t, 3H); 1.2 (t, 3H); 1.8 (m, 1H); 2.1 (m, 1H); 2.4 (s, 6H); 3.4 (t, 1H); 4.1 (q, 2H); 5.0 (s, 2H); 6.9 (m, 2H); 7.15-7.30 (m, 5H).

Step D: Preparation of 2-(3-(2,6-Dimethylbenzyloxy)phenyl)-2-ethylacetic Acid

To a stirred solution of Ethyl 2-(3-(2,6-dimethylbenzyloxy)phenyl)-2-ethylacetate (Step C, 3.26 g, 10.0 mmol) in absolute ethanol (60 ml) was added 1N NaOH (20 ml) at room temperature. The reaction mixture was stirred for 3 hours, acidified by 1N HCl, and concentrated. The residue was taken into chloroform and washed with 1N HCl, brine, dried over $Na_2SO_4$, filtered, concentrated and purified by flash chromatography on a silica gel column (chloroform:methanol 95:5 spiked with acetic acid) to give the title compound.
$^1$H NMR (270 MHz, $CDCl_3$): 0.9 (t, 3H); 1.8 (m, 1H); 2.1 (m, 1H); 2.4 (s, 6H); 3.4 (t, 1H); 5.0 (s, 2H); 6.9 (m, 2H); 7.15-7.30 (m, 5H).

Example 3

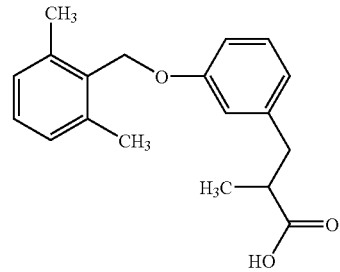

3-(3-(2,6-Dimethylbenzyloxy)phenyl)-2-methylpropanoic Acid

Step A: Preparation of Ethyl 3-(3-hydroxyphenyl)propanoate

A solution of 3-Hydroxyphenylpropanoic acid (25 g, 150.60 mmol) and p-Toluenesulfonic acid monohydrate (3.80 g, 20 mmol) in abs ethanol (250 ml) was refluxed for 4 hours or until all the starting material is consumed. The reaction mixture was concentrated, diluted with ethyl acetate and washed with water. The organic layer was dried over $Na_2SO_4$, filtered, concentrated, and purified by flash chromatography on a silica gel column (hex:ethyl acetate 2:1) to give the title compound.

$^1$H NMR (270 MHz, $CDCl_3$): 1.2 (t, 3H); 2.6 (t, 2H); 2.8 (t, 2H); 4.2 (q, 2H); 6.7-6.8 (m, 3H); 7.2 (m, 1H).

Step B: Preparation of Ethyl 3-(2,6-dimethylbenzyloxy)phenyl)propanoate

A solution of 2,6-Dimethylbenzyl alcohol (7.71 g, 56.7 mmol) and diisopropyl azodicarboxylate (DIAD, 11.36 g, 56.18 mmol) in THF (30 ml) and DMF (13 ml) was added drop wise to a solution of Ethyl 3-(3-hydroxyphenyl)propanoate (Step A, 10.0 g, 51.5 mmol) and triphenylphosphine (14.73 g, 56.18 mmol) in THF (100 ml) at 0° C. The reaction mixture was stirred at the same temperature for 4 hours, diluted with ether and washed with water. The organic layer was dried over $Na_2SO_4$, filtered, concentrated, and purified by flash chromatography on a silica gel column (hex:ethyl acetate 4:1) to give the title compound.

$^1$H NMR (270 MHz, $CDCl_3$): 1.2 (t, 3H); 2.4 (s, 6H); 2.6 (t, 2H); 3.0 (t, 2H); 4.2 (q, 2H); 5.1 (s, 2H); 6.8 (m, 3H); 7.2-7.4 (m, 4H).

Step C: Preparation of Ethyl 3-(3-(2,6-dimethylbenzyloxy)phenyl)-2-methylpropanoate To a stirred solution of Ethyl 3-(2,6-dimethylbenzyloxy)phenylacetate (Step B, 4.53 g, 14.5 mmol) in dry THF (30 ml) at −68° C. under a dry argon atmosphere was added LiHMDS drop wise (1 M solution in THF, 21.77 ml, 21.77 mmol), and the resulting orange solution was stirred at low temperature for 30 minutes before $CH_3I$ (20.60 g, 145.2 mmol) was added. The reaction mixture was slowly warmed to room temperature and stirred for 15 hours. The reaction was quenched with ice, and the product was extracted with EtOAc (2×), the organic phase was washed with brine, dried over $Na_2SO_4$, filtered, concentrated and purified by flash chromatography on a silica gel column (hex:ether 5:1) to give the title compound.

$^1$H NMR (270 MHz, $CDCl_3$): 1.2 (t, 3H); 1.5 (t, 3H); 2.4 (s, 6H); 2.51-2.58 (m, 1H); 2.71 (dd, 1H); 2.88 (dd, 1H); 4.2 (q, 2H); 5.1 (s, 2H); 6.9 (m, 3H); 7.2-7.4 (m, 4H).

Step D: Preparation of 3-(3-(2,6-Dimethylbenzyloxy)phenyl)-2-methylpropanoic Acid To a stirred solution of Ethyl 3-(3-(2,6-dimethylbenzyloxy)phenyl)-2-methylpropanoate (Step C, 1.61 g, 4.9 mmol) in absolute ethanol (25 ml) was added 1N NaOH (10 ml) at room temperature. The reaction mixture was stirred for 3 hours, acidified to pH 3.5-4.0 by 1N HCl, and concentrated. The residue was taken into chloroform and washed with 0.1N HCl, brine, dried over $Na_2SO_4$, filtered, concentrated and purified by flash chromatography on a silica gel column (chloroform:methanol 95:5 spiked with acetic acid) to give the title compound.

$^1$H NMR (270 MHz, $CDCl_3$): 1.5 (t, 3H); 2.4 (s, 6H); 2.51-2.58 (m, 1H); 2.71 (dd, 1H); 2.88 (dd, 1H); 5.1 (s, 2H); 6.9 (m, 3H); 7.2-7.4 (m, 4H).

For all of the biological activity examples that follow, Compound CW was produced in accordance with chemical synthesis Example 1.

BIOLOGICAL ACTIVITY EXAMPLES

Example A

Antidiabetic Effects of Compound CW in db/db Mice db/db mice have a defect in leptin signaling, leading to hyperphagia, obesity and diabetes. Moreover, unlike ob/ob mice on a C57BL/6J background, db/db mice on a C57BLKS background undergo failure of their insulin-producing pancreatic islet cells, resulting in progression from hyperinsulinemia (associated with peripheral insulin resistance) to hypoinsulinemic diabetes.

Male obese (db/db homozygote) C57BL/Ksola mice approximately 8 weeks of age, were obtained from Jackson Labs (Bar Harbor, Me.) and randomly assigned into groups of 5-7 animals such that the body weights (40-45 g) and serum glucose levels ($\geq$300 mg/dl in fed state) were similar between groups; male lean (db/+ heterozygote) mice served as cohort controls. A minimum of 7 days was allowed for adaptation after arrival. All animals were maintained under controlled temperature (23° C.), relative humidity (50±5%) and light (7:00-19:00), and allowed free access to standard chow (Formulab Diet 5008, Quality Lab Products, Elkridge, Md.) and water.

Mice received daily oral doses of vehicle or Compound CW for 2 weeks. At the end of the treatment period 100 µl of venous blood was withdrawn in a heparinized capillary tube from the retro-orbital sinus for serum chemistry analysis. Mice were in the fed state at the time of blood sampling.

After 2 weeks of daily oral dosing, Compound CW elicited a significant reduction in blood glucose (Table 1). Similarly, Compound CW reduced serum triglycerides (Table 2).

TABLE 1

Effect of Compound CW on serum glucose in the db/db mouse model of type II diabetes

| Groups | Glucose mg/dL |
|---|---|
| Vehicle (Control) | 735 ± 66 |
| COMPOUND CW – 100 mg/kg | 171 ± 66* |

*p < 0.05 significantly different compared with vehicle-control

TABLE 2

Effect of Compound CW on serum triglycerides in db/db mice

| Group | Triglycerides ± SEM (mg/dL) |
|---|---|
| Vehicle | 221 ± 62 |
| COMPOUND CW | 109 ± 13 |

Example B

Activity of Compound CW on Human PPARα

In order to examine the activity of Compound CW on PPARα, a transactivation assay was used. Transactivation assays take advantage of the modular domain structure of nuclear receptors. A fusion protein was made between the human or mouse PPAR ligand binding domain (PPAR-LBD) and the yeast Gal4 DNA binding domain ("activator plasmid"). The reporter gene construct consisted of the Gal4 DNA binding element in cis with a luciferase reporter. When an agonist binds the Gal4/PPAR-LBD, the fusion protein binds the Gal4 DNA binding element on the reporter gene resulting in transcription of the firefly luciferase gene. Luciferase oxidizes the substrate luciferin in an ATP-dependent reaction; the amount of light given off is a direct measure of the level of the enzyme and, consequently, of the activity of the ligand binding the PPAR-LBD.

The activator expressing plasmids contained a yeast GAL4 DNA-binding domain fused to the human PPARα ligand binding and hinge domains (a.a. 167-468). The reporter plasmid used was pFRLuc, which has the firefly luciferase gene under the control of a GAL4 UAS containing promoter (Stratagene (La Jolla, Calif.)).

One day prior to transfection, cells were seeded in 24-well plates at a density of $5 \times 10^4$-$2 \times 10^5$ cells/well, depending upon the cell type. Cells were transfected using Lipofectamine 2000 reagent (Invitrogen (Calsbad, Calif.)). Lipofectamine 2000 was added (2.5 μL/well) to a tube containing 50 μL of Optimem media. In a second tube, plasmid DNA was added at a ratio of 4:3 (reporter:activator); where appropriate, salmon sperm DNA was substituted for activator expressing plasmid to yield a total of 0.8 μg DNA/well. The DNA was added to 50 μL of Optimem Reduced Serum media (without added serum).

The two solutions were incubated at room temperature for 5 minutes, and then combined. The combined solution was incubated at room temperature for an additional 30 minutes to form the liposome complex.

Cells were washed once with PBS, and 100 μL of transfection mix added to each well. Plates were incubated at 37° C. in a 5% $CO_2$ incubator for approximately 4 hr, followed by aspiration of the transfection mix and replacement of the medium with fresh Eagle's minimum essential medium (EMEM (Cambrex (East Rutherford, N.J.)) supplemented with 10% FBS and glutamine "EMEM complete"). 24 hr post-transfection, the plates were treated with the appropriate compounds in EMEM complete media. 24 hours after treatment, the cells were washed once with PBS and 100 μL/well of reporter lysis buffer (Promega (Madison, Wis.)) was added. Cells were freeze/thawed once prior to analysis. Approximately 10 μL of lysate was added to 100 μL of firefly luciferase substrate.

The results show that PN2069 is a partial agonist on human PPARα (in the same experiment, the positive control Wy-14,643 reached maximal activity of ~40,000 RLU). See FIG. 1.

What is claimed is:

1. A biologically active agent, wherein the agent is a compound of the formula:

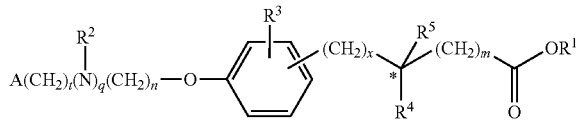

Formula I wherein n is 1;

one of m and x is 0 and the other is 0, 2, or 4;

q is 0;

t is 0;

$R^3$ is hydrogen, halo, alkyl having from 1 to 3 carbon atoms, or alkoxy having from 1 to 3 carbon atoms;

one of $R^4$ and $R^5$ is alkyl having 1 carbon atom and the other is hydrogen;

A is 2,6-dimethylphenyl; and $R^1$ is hydrogen or alkyl having 1 or 2 carbon atoms;

or when $R^1$ is hydrogen, a pharmaceutically acceptable salt of the compound.

2. The biologically active agent of claim 1, wherein $R^3$ is hydrogen.

3. The biologically active agent of claim 2, wherein the compound is 2-(3-(2,6-Dimethylbenzyloxy)-phenyl)-2-methylacetic acid.

\* \* \* \* \*